United States Patent
Kirschning et al.

(10) Patent No.: US 9,458,234 B2
(45) Date of Patent: *Oct. 4, 2016

(54) TLR2 ANTAGONISTIC ANTIBODY AND USE THEREOF

(71) Applicants: Technische Universitat Munchen, Munich (DE); Amgen Inc., Thousand Oaks, CA (US)

(72) Inventors: Carsten Juergen Kirschning, Essen (DE); Guangxun Meng, Shanghai (CN); Hermann Wagner, Eching (DE)

(73) Assignees: Technische Universitat Munchen, Munich (DE); Amgen Inc., Thousand Oaks, CA (US)

( * ) Notice: Subject to any disclaimer, the term of this patent is extended or adjusted under 35 U.S.C. 154(b) by 43 days.

This patent is subject to a terminal disclaimer.

(21) Appl. No.: 14/134,569

(22) Filed: Dec. 19, 2013

(65) Prior Publication Data
US 2014/0343256 A1    Nov. 20, 2014

Related U.S. Application Data

(63) Continuation of application No. 10/595,204, filed as application No. PCT/EP2004/010700 on Sep. 23, 2004, now Pat. No. 8,623,353.

(30) Foreign Application Priority Data

Sep. 23, 2003  (EP) ..................... 03021461

(51) Int. Cl.
| | |
|---|---|
| A61K 39/395 | (2006.01) |
| C07K 16/00 | (2006.01) |
| C07K 16/28 | (2006.01) |
| C12N 1/00 | (2006.01) |
| C12N 5/10 | (2006.01) |
| C07K 14/705 | (2006.01) |
| A61K 39/00 | (2006.01) |

(52) U.S. Cl.
CPC .......... *C07K 16/28* (2013.01); *C07K 16/2896* (2013.01); *A61K 39/3955* (2013.01); *A61K 2039/505* (2013.01); *C07K 2316/96* (2013.01); *C07K 2317/33* (2013.01); *C07K 2317/51* (2013.01); *C07K 2317/515* (2013.01); *C07K 2317/56* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,530,101 A | 6/1996 | Queen et al. |
| 8,623,353 B1 | 1/2014 | Kirschning et al. |
| 2005/0265998 A1 | 12/2005 | Elson |
| 2006/0165686 A1 | 7/2006 | Elson et al. |

FOREIGN PATENT DOCUMENTS

| | | |
|---|---|---|
| WO | WO 01/36488 A1 | 5/2001 |
| WO | WO 03/070761 A1 | 8/2003 |

OTHER PUBLICATIONS

Abcam technical datasheet for TL2.1; 4 pages; downloaded Apr. 16, 2010 from www.abcam.com/TLR2-antibody-TL-2-1-ab9100.html.
Aliprantis et al., Cell activation and apoptosis by bacterial lipoproteins through toll-like receptor-2. Science. Jul. 30, 1999;285(5428):736-9.
Bork et al., Go hunting in sequence databases but watch out for the traps. Trends Genet. Oct. 1996;12(10):425-7.
Bork, Powers and pitfalls in sequence analysis: the 70% hurdle. Genome Res. Apr. 2000;10(4):398-400.
Brenner, Errors in genome annotation. Trends Genet. Apr. 1999;15(4):132-3.
Brightbill et al., Host defense mechanisms triggered by microbial lipoproteins through toll-like receptors. Science. Jul. 30, 1999;285(5428):732-6.
Cario, Barrier-protective function of intestinal epithelial Toll-like receptor 2. Mucosal Immunol. Nov. 2008;1 Suppl 1:S62-6.
Daniel et al., Mapping of linear antigenic sites on the S glycoprotein of a neurotropic murine coronavirus with synthetic peptides: a combination of nine prediction algorithms fails to identify relevant epitopes and peptide immunogenicity is drastically influenced by the nature of the protein carrier. Virology. Aug. 1, 1994;202(2):540-9.
Doerks et al., Protein annotation: detective work for function prediction. Trends Genet. Jun. 1998;14(6):248-50.
Kaufman et al., Transgenic analysis of a 100-kb human beta-globin cluster-containing DNA fragment propagated as a bacterial artificial chromosome. Blood. Nov. 1, 1999;94(9):3178-84.
Lederman et al., A single amino acid substitution in a common African allele of the CD4 molecule ablates binding of the monoclonal antibody, OKT4. Mol Immunol. Nov. 1991;28(11):1171-81.
Li et al., Beta-Endorphin omission analogs: dissociation of immunoreactivity from other biological activities. Proc Natl Acad Sci U S A. Jun. 1980;77(6):3211-4.
Lifespan Biosciences technical datasheet for LS-C90537; 1 page; printed Apr. 15, 2010.
Matsuguchi et al., Gene expressions of lipopolysaccharide receptors, toll-like receptors 2 and 4, are differently regulated in mouse T lymphocytes. Blood. Feb. 15, 2000;95(4):1378-85.

(Continued)

*Primary Examiner* — Bridget E Bunner
(74) *Attorney, Agent, or Firm* — Wolf, Greenfield & Sacks, P.C.

(57) ABSTRACT

The present invention is directed to a cross-reactive antibody, which specifically inhibits or blocks the mammalian Toll-like receptor 2 (TLR2)-mediated immune cell activation. The invention is further directed to an isolated nucleic acid or vector coding for the variable regions of the heavy and/or light chain of the antibody. It is further providing a pharmaceutical composition comprising the antibody, nucleic acid or vector and is directed to the use of the composition in the prevention and/or treatment of inflammatory processes or any other process induced by bacterial infection, trauma, or chronic inflammation, or for the prevention and/or treatment of bacteriaemia or sepsis.

18 Claims, 21 Drawing Sheets

(56) References Cited

OTHER PUBLICATIONS

McCormack et al., Toll-like receptors and NOD-like receptors in rheumatic diseases. Arthritis Res Ther. 2009;11(5):243. Epub Oct. 14, 2009.

Meng et al., Antagonistic antibody prevents toll-like receptor 2-driven lethal shock-like syndromes. J Clin Invest. May 2004;113(10):1473-81.

Ngo et al., Computational complexity, protein structure prediction, and the Levinthal paradox. The Protein Folding Problem and Tertiary Structure Prediction. pp. 492-495. 1994.

Phillips et al., The challenge of gene therapy and DNA delivery. J Pharm Pharmacol. Sep. 2001;53(9):1169-74.

Sandor et al., Importance of extra- and intracellular domains of TLR1 and TLR2 in NFkappa B signaling. J Cell Biol. Sep. 15, 2003;162(6):1099-110.

Skolnick et al., From genes to protein structure and function: novel applications of computational approaches in the genomic era. Trends Biotechnol. Jan. 2000;18(1):34-9.

Smith et al., The challenges of genome sequence annotation or "The devil is in the details". Nat Biotechnol. Nov. 1997;15(12):1222-3.

Uehori et al., Simultaneous blocking of human Toll-like receptors 2 and 4 suppresses myeloid dendritic cell activation induced by *Mycobacterium bovis* bacillus Calmette-Guérin peptidoglycan. Infect Immun. Aug. 2003;71(8):4238-49.

Uniprot Accession No. Q9QUN7; 9 pages; Mar. 23, 2010.

Wang et al., Rapid analysis of gene expression (RAGE) facilitates universal expression profiling. Nucleic Acids Res. Dec. 1, 1999;27(23):4609-18.

Wells et al., Additivity of mutational effects in proteins. Biochemistry. Sep. 18, 1990;29(37):8509-17.

Filled, 2nd Ab alone; Thin line, TL2.1; Thick line, mT2.5.

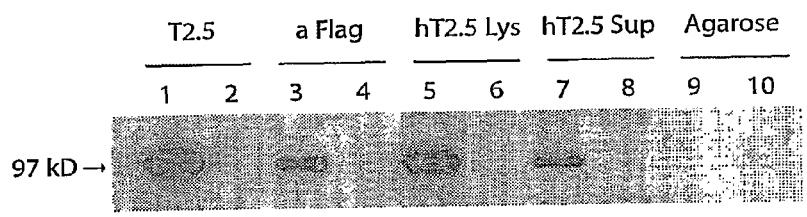

Abs for IP, as indicated, hT2.5 stands for lineralized T2.5 heavy chain and light chain fused with C terminal human IgG1 Fc.

Ags for IP, for lanes 1, 3, 5, 7, 9, it was lysates from HEK 293 cells over expressing Flag taged mouse TLR2 for lanes 2, 4, 6, 8, 10, it was lysates from HEK293 cells without any transfection.

WB was done with anti Flag poly clonal sera. Binds at 97 kD resolved on 10 % SDS-PAGE gel indicate the position of Flag taged murine TLR2 upon overexpression in HEK 293 cells precipated with Abs.

Fig 16

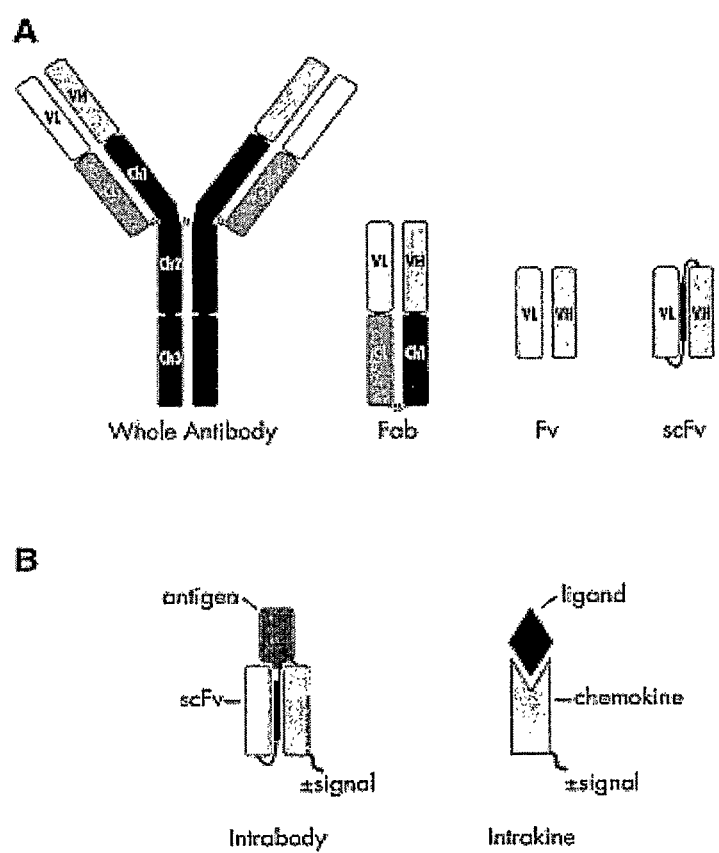
Fig. 16 A1

Figure 2:
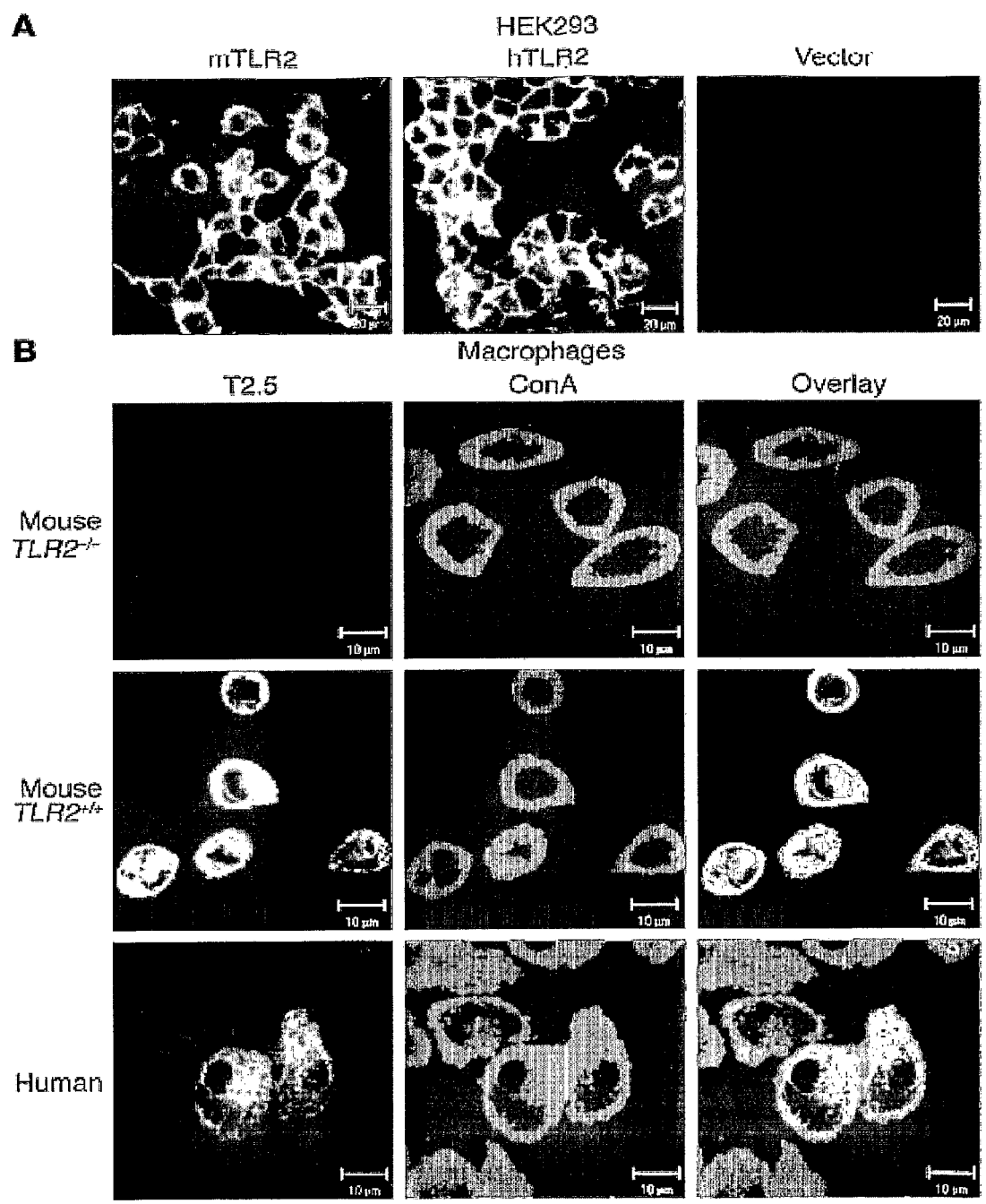

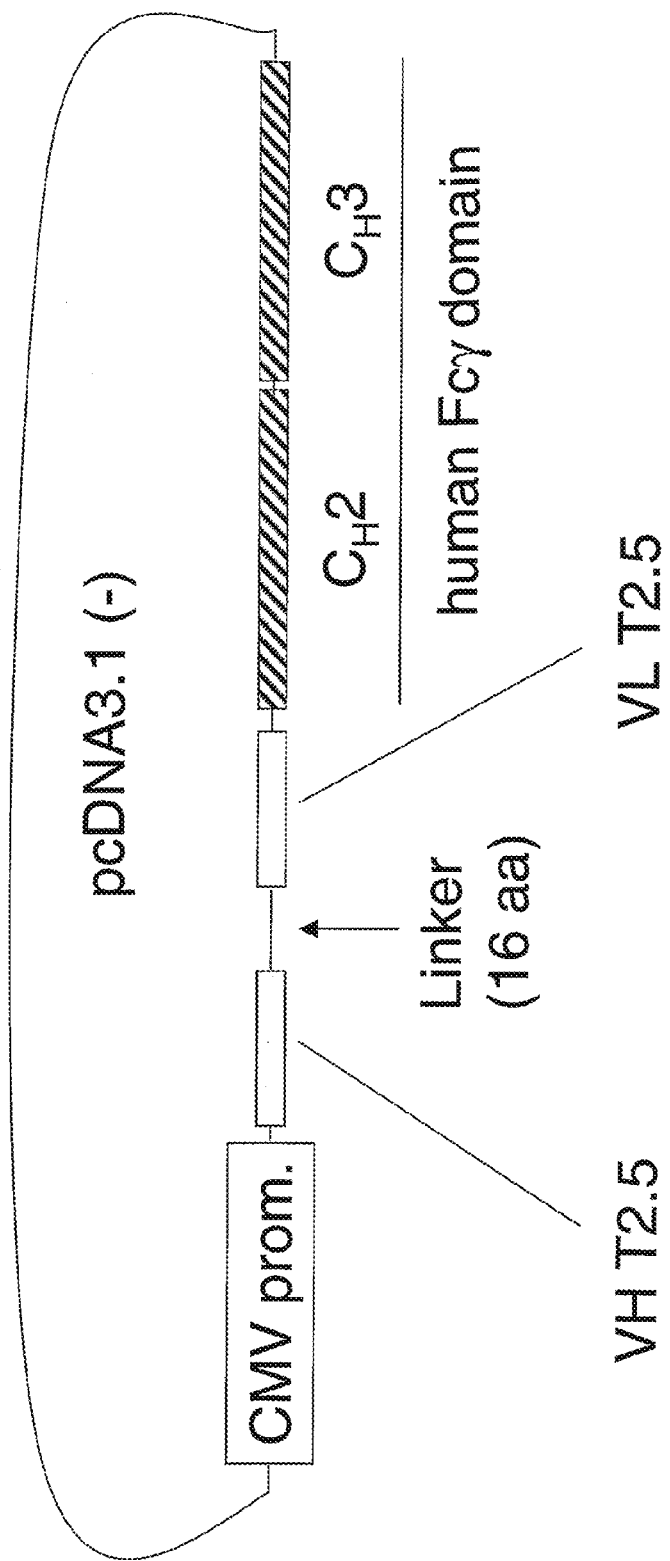
Fig. 16A2
Expression construct for single chain and partially humanized anti TLR2 antibody

Figure 3:
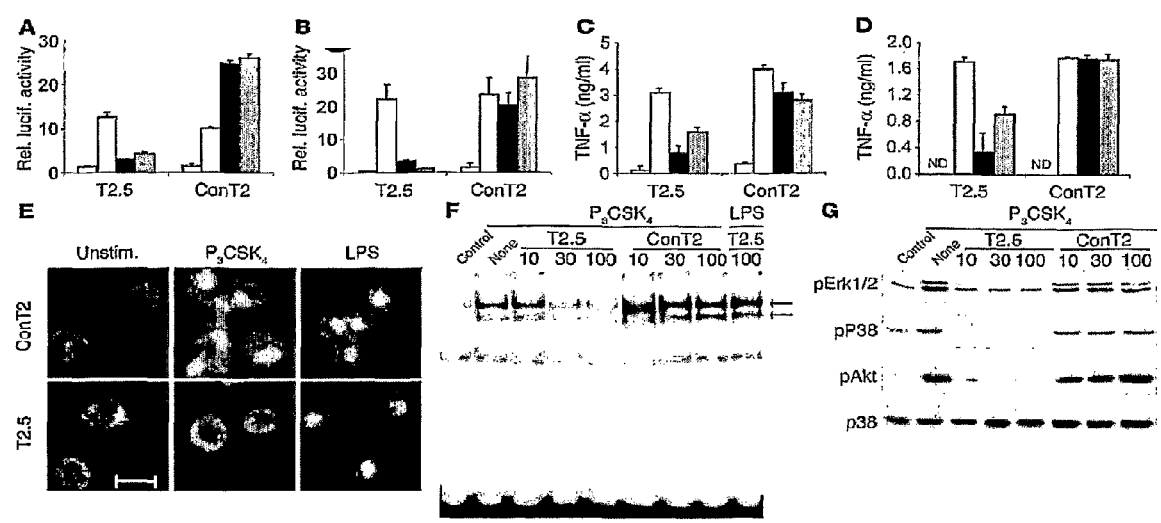

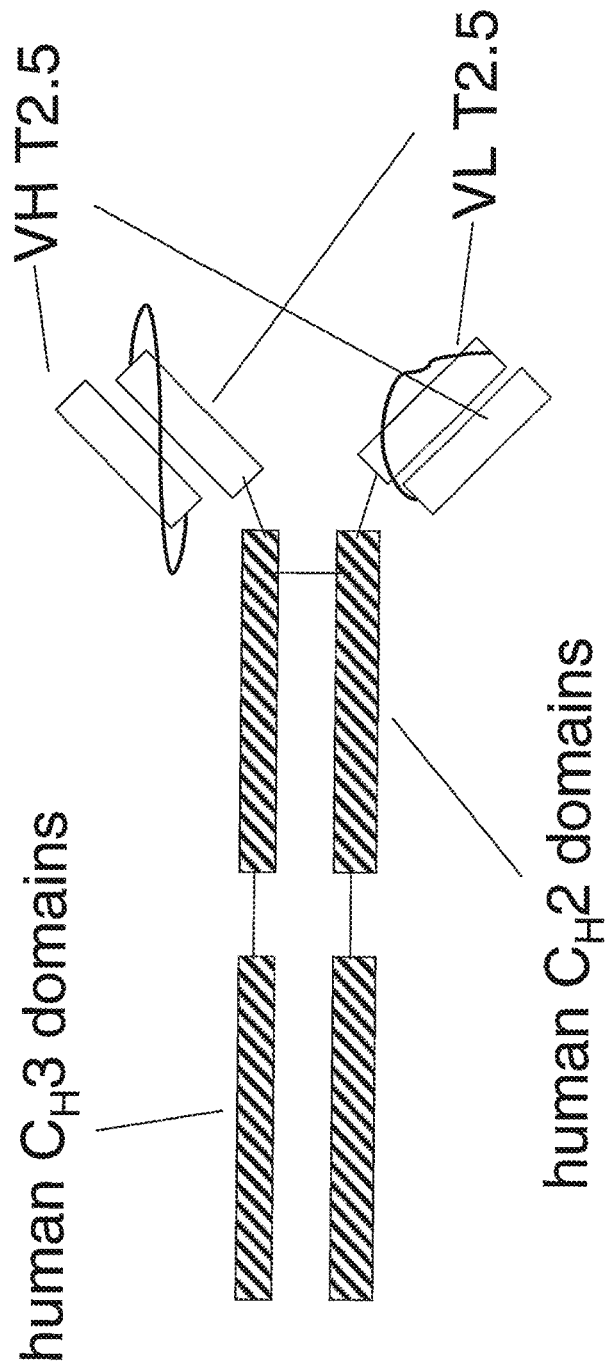
Fig. 16A3
Partially humanized anti TLR2 Ab

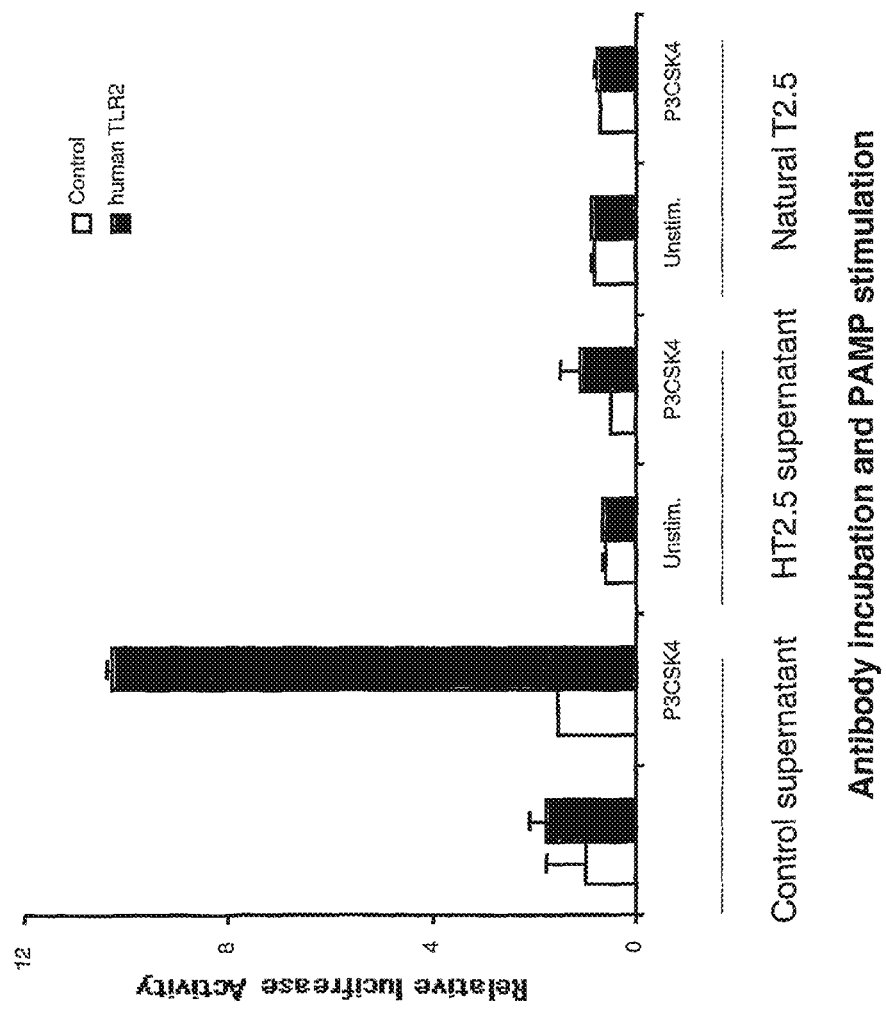

TLR2 ANTAGONISTIC ANTIBODY AND USE THEREOF

RELATED APPLICATIONS

This application is a continuation of U.S. patent application Ser. No. 10/595,204, filed Jan. 25, 2008, now U.S. Pat. No. 8,623,353, which application is a national stage filing under 35 U.S.C. §371 of international application PCT/EP2004/010700, filed Sep. 23, 2004, which was published under PCT Article 21(2) in English, the entire contents of which are incorporated herein by reference.

The present invention is directed to a cross-reactive antibody, which specifically inhibits or blocks the mammalian Toll-like receptor 2 (TLR2)-mediated immune cell activation. The invention is further directed to an isolated nucleic acid or vector coding for the variable regions of the heavy and/or light chain of said antibody. It is further providing a pharmaceutical composition comprising said antibody, nucleic acid or vector and is directed to the use of said composition in the prevention and or treatment of inflammatory processes or any other process induced by bacterial infection, trauma, or chronic inflammation, or for the prevention and/or treatment of bacteriaemia or sepsis.

Host cells recognize specific patterns of microbial components through Toll-like receptors (TLRs) which are crucial in mediating innate immune responses[1,2]. Lipopolysaccharide (LPS) from the outer membrane of Gram-negative bacteria is a potent agonist for TLR4 whose effects on the host organism have been studied extensively in experimental models of infection and septic shock[3-5]. Over-stimulation of host immune cells by microbial products accompanied by the release of large amounts of inflammatory mediators is recognized as a major cause of septic shock[6-9].

Indeed, this concept has been validated by using both gene targeted mice lacking the expression of the respective receptors, and by receptor specific inhibition of microbial product induced host cell activation. For example, the non-redundant role of CD14 as an important element of a cellular LPS recognition system has been demonstrated by application of inhibitory anti CD14 antibodies in rabbits[10,11]. The blockade of LPS receptors or extracellular effector proteins as the earliest possible targets of therapeutic strategies was shown to be preventive[12]. Another approach of therapeutic intervention in septic shock has been interference with the functions of proinflammatory cytokines such as TNFα or IL-1β. For instance, competitive inhibition of cytokine binding to its signaling receptors by application of recombinant extracellular domain (ECD) or naturalizing receptor antagonist proteins have been shown to be protective in LPS induced shock in rats[13]. In addition, antagonistic antibodies targeting cytokines or ECDs of its receptors have been tested[14]. While cytokine blockade for therapeutic intervention in acute infections (sepsis) has been disappointing[15], its use in treatment of chronic inflammations is promising[16,17].

Besides Gram-negative, Gram-positive bacteria lacking LPS play an important role in the clinical manifestation of shock[8]. Cell wall components from these bacteria such as peptidoglycan (PGN) and lipoteichoic acid (LTA) are considered the main causative agents of Gram-positive shock[18,19]. PGN is a main component of Gram-positive, but also of other bacterial cell walls, and consists of an alternating β (1,4) linked N-acetylmuramyl and N-acetylglucosaminyl glycan cross linked by small peptides[20]. In contrast, the macroamphiphile LTA, a saccharide chain molecule consisting of repetitive oligosaccharides connected by alcohols such as ribitol and carrying acyl chains through which it is anchored to the bacterial cytoplasmic membrane, is specific for Gram-positive bacteria[21]. For example, LTA has been described to carry the major stimulatory activity of *Bacillus subtilis*[22]. The stimulatory properties of tripalmityolated proteins whose production is not restricted to Gram-negative or Gram-positive bacteria are mimicked by the synthetic compound N-palmitoyl-S-(2,3-bis(palmitoyloxy)-(2R,S)-propyl)-(R)-cysteinyl-seryl-(lysyl)-3-lysine ($P_3CSK_4$)[23].

Most of these bacterial products are known to activate innate immune cell responses by triggering the TLR2 signaling cascade[2]. The TLR2ECD, whose N-terminal portion has been implicated in PGN recognition[24], contains an array of distinct leucine rich repeat (LRR) motifs[25]. The LRR rich domain is followed by an LRR C-terminal (LRRCT), a trans-membrane, and an intracellular C-terminal Toll-IL-1 receptor-plant disease resistance protein (TIR) domain[25].

WO 01/36488 generally describes an anti-TLR2 antibody. It is further described to prepare such an antibody by using a TLR2 immunogen, for example a part of the TLR2 molecule, for example a domain (e.g. the extracellular domain) or a shorter peptide or polypeptide sequence e.g. an epitopic sequence. However, it is indicated in WO 01/36488 that it is preferred for the immunogen to be one which mimics the natural protein as far as possible.

WO 01/36488 in particular obtains and discloses a monoclonal antibody having particular properties and characteristics (e.g. binding and inhibition characteristics). This antibody is called, "Mab TL2.1". The hybridoma producing this antibody was deposited under the terms of the Budapest Treaty at the European Collection of Cell Cultures (ECACC) on Oct. 28, 1999 under the Accession No. 99102832. This antibody is the only precise and fully disclosed Example for an antibody presented in WO 01/36488.

The inventors conducted some research work and tested Mab TL2.1 for its characteristics and it turned out that this antibody is not cross-reactive between different mammalian species.

Therefore, it is the objective problem underlying the present invention to provide a cross-reactive antibody, which specifically inhibits or blocks the mammalian Toll-like receptor 2 (TLR2)-mediated immune cell activation by specifically binding to the highly conserved C-terminal portion of the extracellular domains of TLR2. It is further an objective problem of the present invention to provide an antibody which is capable of prevention and/or treatment of bacteriaemia or sepsis, or of prevention and/or treatment of inflammatory processes or any other process induced by bacterial infection, trauma, or chronic inflammation. Additionally, a problem underlying the invention is to provide an improved approach of gene therapy, based on an overexpression of the antibody or a functional part thereof in a host organism in order to achieve the above mentioned therapeutic effect.

These objects are solved by the subject-matters of the independent claims. Preferred embodiments are set forth in the dependent claims.

Herein, it is shown that a murine monoclonal antibody (mAb) raised against the murine TLR2 extracellular domain (=ECD) inhibits TLR2 mediated activation of murine and human cells. The protective potential of neutralizing TLR2 with this antibody was demonstrated in vivo using two TLR2 dependent shock models. Thus, antibody targeting of the TLR2ECD is a valuable strategy to prevent TLR2 driven septic shock.

In this invention, for the first time a cross-reactive antibody is described, which is capable of inhibiting or blocking the mammalian Toll-like receptor 2 (TLR2)-mediated immune cell activation by specifically binding to the C-terminal portion of the extracellular domains of at least human and murine TLR2. The cross-reactivity of the antibody of the invention in particular was shown by specificity for the human and murine TLR2 sequences. Thus, the antibody of the present invention for the first time is capable of specifically binding to the highly conserved TLR2 sequence shared among most mammals, in particular among mice and human beings.

It is noted that according to experimental data obtained by the inventors, the presently known antibodies as disclosed in WO 01/36488 (TL2.1) interact with human TLR2 and an unspecific antigen from murine cells in FACS analysis and immunocytochemical staining analysis whereas the antibody of the present invention (e.g. T2.5) specifically recognizes both murine and human TLR2, therefore being cross-reactive. The respective experimental data are provided in the Figures and the Examples.

The present invention in particular is directed to the following aspects and embodiments:

According to a first aspect, the present invention is directed to a cross-reactive antibody, which specifically inhibits or blocks the mammalian Toll-like receptor 2 (TLR2)-mediated immune cell activation by specifically binding to the C-terminal portion of the extracellular domains of at least human and murine TLR2.

As mentioned above, the antibody of the present invention is defined as being cross-reactive as an essential feature. The term "cross-reactive" as used herein refers to the ability of an individual antibody to react with an antigenic determinant within the TLR2 orthologue products of two different species (here: human and murine). Cross reactivity in the meaning of the present invention arises because one specific antigen has an epitope which is structurally similar to the analogous epitope within the analogous protein of two species. As mentioned above, an example of cross-reactivity in the meaning of the present invention is the capability of an anti-TLR2 antibody to specifically bind to the C-terminal portion of the extracellular domains of at least human and murine TLR2 which is preferably encompassing a region from amino acids T221 to R587 (for the corresponding sequence information it is referred to Genebank accession number HSU 88878) or a subregion thereof.

The term extracellular domain is used herein as commonly defined in the corresponding field of science, i.e. as usually defined in the field of type I transmembrane receptors. Those are proteins that span the thickness of the plasma membrane of the cell, with one end of the receptor outside (extracellular domain) and one inside (intracellular domain) the cell. Both are connected by the transmembrane domain.

The antibody of the present invention is, according to an embodiment, a polyclonal antibody, a monoclonal antibody, a humanized antibody, a chimeric antibody, or a synthetic antibody.

The term "antibody", is used herein for intact antibodies as well as antibody fragments, which have a certain ability to selectively bind to an epitop. Such fragments include, without limitations and as an example, Fab, F(ab')$_2$ und Fv antibody fragment. The term "epitop" means any antigen determinant of an antigen, to which the paratop of an antibody can bind. Epitop determinants usually consist of chemically active surface groups of molecules (e.g. amino acid or sugar residues) and usually display a three-dimensional structure as well as specific physical properties.

The antibodies according to the invention can be produced according to any known procedure. For example, the pure complete TLR2ECD or a part of it can be produced and used as immunogen, to immunize an animal and to produce specific antibodies.

The production of polyclonal antibodies is commonly known. Detailed protocols can be found for example in Green et al, Production of Polyclonal Antisera, in *Immunochemical Protocols* (Manson, editor), pages 1-5 (Humana Press 1992) und Coligan et al, Production of Polyclonal Antisera in Rabbits, Rats, Mice and Hamsters, in *Current Protocols In Immunology*, section 2.4.1 (1992). In addition, the expert is familiar with several techniques regarding the purification and concentration of polyclonal antibodies, as well as of monoclonal antibodies (Coligan et al, Unit 9, *Current Protocols in Immunology*, Wiley Interscience, 1994).

The production of monoclonal antibodies is as well commonly known. Examples include the hybridoma method (Kohler and Milstein, 1975, Nature, 256:495-497, Coligan et al., section 2.5.1-2.6.7; and Harlow et al., *Antibodies: A Laboratory Manual*, page 726 (Cold Spring Harbor Pub. 1988)), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

In brief, monoclonal antibodies can be attained by injecting a mixture which contains the protein in question into mice. The antibody production in the mice is checked via a serum probe. In the case of a sufficient antibody titer, the mouse is sacrificed and the spleen is removed to isolate B-cells. The B cells are fused with myeloma cells resulting in hybridomas. The hybridomas are cloned and the clones are analyzed. Positive clones which contain a monoclonal antibody against the protein are selected and the antibodies are isolated from the hybridoma cultures. There are many well established techniques to isolate and purify monoclonal antibodies. Such techniques include affinity chromatography with protein A sepharose, size-exclusion chromatography and ion exchange chromatography. Also see for example, Coligan et al, section 2.7.1-2.7.12 and section, "Immunglobulin G (IgG)", in *Methods In Molecular Biology*, volume 10, pages 79-104 (Humana Press 1992).

According to a preferred embodiment, the antibody of the invention specifically binds through its variable regions of the heavy- and light chain, which regions carry the amino acid sequence as depicted in SEQ ID NO:1 and/or 2, or a variant thereof. The term "variant" as used in this connection is explained in detail below (regarding the aspect directed to the nucleic acid of the invention).

Methods of making such antibody fragments, and synthetic and derivatised antibodies are well known in the art. Also included in the scope of the term, "antibody" as used herein (in addition to the ones indicated above) are antibody fragments containing the complementarity-determining regions (CDRs) or hypervariable regions of the antibodies. These may be defined as the region comprising the amino acid sequences on the light and heavy chains of an antibody which form the three-dimensional loop structure that contributes to the formation of the antigen binding site. CDRs may be used to generate CDR-grafted antibodies. The term "CDR grafted" defines an antibody having an amino acid sequence in which at least parts of one or more sequences in the light and/or variable domains have been replaced by analogous parts of CDR sequences from an antibody having a different binding specificity for a given antigen.

One of skill in the art can readily produce such CDR grafted antibodies using methods well known in the art (see Borrebaeck, Antibody Engineering: A Practical Guide, W. H. Freeman and Company, New York, 1992).

A chimeric antibody of the present invention may be prepared by combining the variable region of an anti TLR2 antibody (or a part thereof) of one species according to the present invention with the constant regions of an antibody derived from a different species. A chimeric antibody may be constructed, for example, according to methods described by Shaw et al., in J. Immun. 1987, 138: 4534 and Sun et al., in PNAS USA, 1987, 84: 214-218.

Monoclonal antibodies and their fragments and derivatives are preferred antibodies according to the present invention.

A further aspect of the invention is thus a hybridoma or cell-line producing an antibody of the invention as defined above.

According to a further embodiment, the antibody of the invention is linked to a pharmaceutical agent and/or to a detectable agent.

In a second aspect, the present invention is directed to an isolated nucleic acid coding for the variable regions of the heavy and/or light chain of the antibody as defined above.

In particular, the invention is directed to an isolated nucleic acid which comprises the sequence of SEQ ID NO: 1 and/or 2 or variants thereof, wherein the variants are each defined as having one or more substitutions, insertions and/or deletions as compared to the sequence of SEQ ID NO: 1 and/or 2, provided that said variants hybridize under moderately stringent conditions to a nucleic acid which comprises the sequence of SEQ ID NO: 1 and/or 2, and further provided that said variants code for an amino acid having activity as a variable region of an antibody specifically binding to the C-terminal portion of the extracellular domains of at least human and murine TLR2 or provided that said variants comprise nucleic acid changes due to the degeneracy of the genetic code, which code for the same or a functionally equivalent amino acid as the nucleic acid sequence of SEQ ID NO: 1 and/or 2.

More preferably, the isolated nucleic acid of the invention comprises at least the sequence of nucleic acids No. 172-201, 244-294 and/or 385-417 of SEQ ID NO: 1, or of nucleic acids No. 130-174, 220-240 and/or 337-363 of SEQ ID NO: 2, or parts thereof. The above mentioned sequences comprise complementarity determining regions (CDR's) 1, 2 and 3, respectively.

Regarding SEQ ID NO: 1, more precisely, nucleic acids No. 172-195, 247-270 and 385-417 or parts thereof are preferred (CDR 1-3), which were identified by application of the IMGT database. Alternatively, nucleic acids 187-201 and 244-294 (CDR 1 and 2) are preferred, identified by the V-BASE database.

Regarding SEQ ID NO: 2, more precisely, nucleic acids No. 139-168, 220-228 and 337-363 or parts thereof are preferred (CDR 1-3), which were identified by application of the IMGT database. Alternatively, nucleic acids 130-174 and 220-240 (CDR 1 and 2) are preferred, identified by the V-BASE database.

A chart comprising SEQ ID NO: 1 and its complementary sequence as well as the encoded amino acids (SEQ ID NO: 6) are depicted below showing the nucleic acid and amino acid sequence of the heavy chain's variable region of the antibody of the invention.

```
                                                               SEQ ID NO: 1
1 to 501
        10         20         30         40         50
ATGTCCTCTC CACAGTCCCT GAAGACACTG ATTCTAACCA TGGGATGGAG
TACAGGAGAG GTGTCAGGGA CTTCTGTGAC TAAGATTGGT ACCCTACCTC
MetSerSer  ProGlnSerLeu LysThrLeu IleLeuThr  MetGlyTrpSer>

60         70         80         90        100
CTGGATCTTT CTCTTCCTCC TGTCAGGAAC TGCAGGTGTC CACTCCCAGG
GACCTAGAAA GAGAAGGAGG ACAGTCCTTG ACGTCCACAG GTGAGGGTCC
TrpIlePhe  LeuPheLeu LeuSerGlyThr AlaGlyVal  HisSerGln>

110        120        130        140        150
TTCAGCTGCA GCAGTCTGGA CCTGAGCTGG TGAACCCTGG GGCGTCAGTG
AAGTCGACGT CGTCAGACCT GGACTCGACC ACTTGGGACC CCGCAGTCAC
ValGlnLeuGln GlnSerGly ProGluLeu ValAsnProGly AlaSerVal>

160        170        180        190        200
AAGTTGTCCT GCAAGGCTTC TGGCTTCACC TTCACAACCT ACGGTATAAA
TTCAACAGGA CGTTCCGAAG ACCGAAGTGG AAGTGTTGGA TGCCATATTT
LysLeuSer  CysLysAlaSer GlyPheThr PheThrThr TyrGlyIleAsn>

210        220        230        240        250
CTGGGTGAAG CAGGGGCCTG GACAGGGACT TGAGTGGATT GGATGGATTT
GACCCACTTC GTCCCCGGAC CTGTCCCTGA ACTCACCTAA CCTACCTAAA
 TrpValLys QlnGlyPro GlyGlnGlyLeu GluTrpIle GlyTrpIle>

260        270        280        290        300
ATCCTAGAGA TGGTAGTACT AACTTCAATG AGAATTTCAA GGACAAGGCC
TAGGATCTCT ACCATCATGA TTGAAGTTAC TCTTAAAGTT CCTGTTCCGG
TyrProArgAsp GlySerThr AsnPheAsn GluAsnPheLys AspLysAla>

310        320        330        340        350
GCATTGACTG TAGACACATC CTCCAGCACA GCGTACATGG AACTCCACAG
CGTAACTGAC ATCTGTGTAG GAGGTCGTGT CGCATGTACC TTGAGGTGTC
AlaLeuThr  ValAspThrSer SerSerThr AlaTyrMet  GluLeuHisSer>

360        370        380        390        400
CCTGACATCT GAAGACTCTG CGGTCTATTT CGTCGAAGA CTGACTGGTG
GGACTGTAGA CTTCTGAGAC GCCAGATAAA GACACGTTCT GACTGACCAC
LeuThrSer  GluAspSer AlaValTyrPhe CysAlaArg LeuThrGly>
```

-continued

```
       410        420        430        440        450
GGACATTCCT TGACTATTGG GGCCAGGGCA CCACTCTCAC AGTCTCCTCA
CCTGTAAGGA ACTGATAACC CCGGTCCCGT GGTGAGAGTG TCAGAGGAGT
GlyThrPheLeu AspTyrTrp GlyGlnGly ThrThrLeuThr ValSerSer>

460        470        480        490        500
GCCAAAACGA CACCCCCATC TGTCTATCCA CTGGCCCCTG GATCTGCTGC
CGGTTTTGCT GTGGGGGTAG ACAGATAGGT GACCGGGGAC CTAGACGACG
AlaLysThr ThrProProSer ValTyrPro LeuAlaPro GlySerAlaAla>

C
G
```

It is noted that the underlined regions are CDR1 and CDR2 sequentially defined by usage of V-BASE database, both nucleic acid and amino acid sequences are underlined accordingly. Italic/bold regions are CDR 1 to 3 defined by application of IMGT database, both nucleic acid and amino acid sequences are marked accordingly (applies also to SEQ ID NO: 2).

Further, a chart comprising SEQ ID NO: 2 and its complementary sequence as well as the encoded amino acids (SEQ ID NO: 7) are depicted below showing the nucleic acid and amino acid sequence of the light chain's variable region of the antibody of the invention.

Furthermore, the whole sequence of the variable region of the heavy chain (including a 5' non coding region) reads as follows:

```
SEQ ID NO: 3:
CATGGACTGAAGGAGTAGAAAGACAACCTATGGCCAATGTCCTCTCCACA

GTCCCTGAAGACACTGATTCTAACCATGGGATGGAGCTGGATCTTTCTCT

TCCTCCTGTCAGGAACTGCAGGTGTCCACTCCCAGGTTCAGCTGCAGCAG

TCTGGACCTGAGCTGGTGAACCCTGGGGCGTCAGTGAAGTTGTCCTGCAA

GGCTTCTGGCTTCACCTTCACAACCTACGGTATAAACTGGGTGAAGCAGG
```

```
                                             SEQ ID NO: 2
1 to 443
        10         20         30         40         50
ATGGAGTCAG ACACACTCCT GCTATGGGTG CTGCTGCTCT GGGTTCCAGG
TACCTCAGTC TGTGTGAGGA CGATACCCAC GACGACGAGA CCCAAGGTCC
MetGluSer AspThrLeuLeu LeuTrpVal LeuLeuThr TrpValProGly>

60         70         80         90        100
CTCCACTGGT GACATTGTGC TCACCCAATC TCCAGCTTCT TTGGCTGTGT
GACCTGACCA CTGTAACACG AGTGGGTTAG AGGTCGAAGA AACCGACACA
SerThrGly AspIleVal LeuThrGlnSer ProAlaSer LeuAlaVal>

110        120        130        140        150
CTCTAGGGCA GAGAGCCACC ATCTCCTGCA GAGCCAGTGA AAGTGTTGAA
GAGATCCCGT CTCTCGGTGG TAGAGGACGT CTCGGTCACT TTCACAACTT
SerLeuGlyGln ArgAlaThr IleSerCys ArgAlaSerGln SerValGlu>

160        170        180        190        200
TATTATGGCA CAAGTTTAAT GCAGTGGTAC AACAGAAAC CAGGACAGCC
ATAATACCGT GTTCAAATTA CGTCACCATG GTTGTCTTTG GTCCTGTCGG
TyrTyrGly ThrSerLeuMet GlnTrpTyr GlnGlnLys ProGlyGlnPro>

210        220        230        240        250
ACCCAAACTC CTCATCTTTG GTGCATCCAA CGTAGAATCT GGGGTCCCTG
TGGGTTTGAG GAGTAGAAAC CACGTAGGTT GCATCTTAGA CCCCAGGGAC
ProLysLeu LeuIlePhe GlyAlaSerAsn ValGluSer GlyValPro>

260        270        280        290        300
TCAGGTTCAG TGGCAGTGGG TCTGGGACAG ACTTCAGCCT CAACATCCAT
AGTCCAAGTC ACCGTCACCC AGACCCTGTC TGAAGTCGGA GTTGTAGGTA
ValArgPheSer GlySerGly SerGlyThr AspPheSerLeu AsnIleHis>

310        320        330        340        350
CCTGTGGAGG AGGATGATAT TGTAATGTAT TTCTGTCAGC AAAGTAGGAA
GGACACCTCC TCCTACTATA ACATTACATA AAGACAGTCG TTTCATCCTT
ProValGlu GluAspAspIle ValMetTyr PheCysGln GlnSerArgLys>

360        370        380        390        400
ACTTCCGTGG ACGTCGGTG GAGGCACCAA GCTGGAAATC AAACGGGCTG
TGAAGGCACC TGCAAGCCAC CTCCGTGGTT CGACCTTTAG TTTGCCCGAC
LeuProTrp ThrPheGly GlyGlyThrLys LeuGluIle LysArgAla>

410        420        430        440
ATGCTGCACC AACTGTATCC ATCTTCCCAC CATCCAGTGA GCA
TACGACGTGG TTGACATAGG TAGAAGGGTG GTAGGTCACT CGT
AspAlaAlaPro ThrValSer IlePhePro ProSerSerGlu Xxx>
```

-continued
GGCCTGGACAGGGACTTGAGTGGATTGGATGGATTTATCCTAGAGATGGT

AGTACTAACTTCAATGAGAATTTCAAGGACAAGGCCGCATTGACTGTAGA

CACATCCTCCAGCACAGCGTACATGGAACTCCACAGCCTGACATCTGAAG

ACTCTGCGGTCTATTTCTGTGCAAGACTGACTGGTGGGACATTCCTTGAC

TATTGGGGCCAGGGCACCACTCTCACAGTCTCCTCAGCCAAAACGACACC

CCCATCTGTCTATCCACTGGCCCCTGGATCTGCTGCC

The whole sequence of the variable region of the light chain (including a 5' non coding region) reads as follows:

SEQ ID NO: 4:
CATGGACTGAAGGAGTAGAAAATCCTCTCATCTAGCTCTCAGAGATGGAG

TCAGACACACTCCTGCTATGGGTGCTGCTGCTCTGGGTTCCAGGCTCCAC

TGGTGACATTGTGCTCACCCAATCTCCAGCTTCTTTGGCTGTGTCTCTAG

GGCAGAGAGCCACCATCTCCTGCAGAGCCAGTGAAAGTGTTGAATATTAT

GGCACAAGTTTAATGCAGTGGTACCAACAGAAACCAGGACAGCCACCCAA

ACTCCTCATCTTTGGTGCATCCAACGTAGAATCTGGGGTCCCTGTCAGGT

TCAGTGGCAGTGGGTCTGGGACAGACTTCAGCCTCAACATCCATCCTGTG

GAGGAGGATGATATTGTAATGTATTTCTGTCAGCAAAGTAGGAAACTTCC

GTGGACGTTCGGTGGAGGCACCAAGCTGGAAATCAAACGGGCTGATGCTG

CACCAACTGTATCCATCTTCCCACCATCCAGTGACCA

The nucleic acid variants according to the invention also comprise nucleic acid fragments which contain more than 10, preferably more than 15, more than 20, more than 25 or more than 30 and up to 50 nucleotides. Most preferably, the fragments comprise the CDR regions as indicated above.

According to the state of the art an expert can test which derivatives and possible variations derived from these revealed nucleic acid sequences according to the invention are, are partially or are not appropriate for specific applications.

Amplification and detection methods are according to the state of the art. The methods are described in detail in protocol books which are known to the expert. Such books are for example Sambrook et al., 1989, Molecular Cloning, A Laboratory Manual, Cold Spring Harbor Press, and all subsequent editions. PCR-methods are described for example in Newton, PCR, BIOS Scientific Publishers Limited, 1994 and all subsequent editions.

As defined above, "variants" are according to the invention especially such nucleic acids, which contain one or more substitutions, insertions and or deletions when compared to the nucleic acids of SEQ ID NO: 1 and 2. These lack preferably one, but also 2, 3, 4, or more nucleotides 5' or 3' or within the nucleic acid sequence, or these nucleotides are replaced by others.

The nucleic acid sequences of the present invention comprise also such nucleic acids which contain sequences in essence equivalent to the nucleic acids described in SEQ ID NO: 1 and 2. According to the invention nucleic acids can show for example at least about 80%, more typically at least about 90% or 95% sequence identity to the nucleic acids described in SEQ ID NO: 1 and 2.

It is noted that the above considerations also apply to SEQ ID NO: 3 and 4.

The term "nucleic acid sequence" means a heteropolymer of nucleotides or the sequence of these nucleotides. The term "nucleic acid", as herein used, comprises RNA as well as DNA including cDNA, genomic DNA and synthetic (e.g. chemically synthesized) DNA and other polymer linked bases such as PNA (peptide nucleic acids).

The invention comprises—as mentioned above—also such variants which hybridize to the nucleic acids according to the invention under moderately stringent conditions.

Stringent hybridization and wash conditions are in general the reaction conditions for the formation of duplexes between oligonucleotides and the desired target molecules (perfect hybrids) or that only the desired target can be detected. Stringent washing conditions mean, e.g., 0.2×SSC (0.03 M NaCl, 0.003 M sodium citrate, pH 7)/10.1% SDS at 65° C. For shorter fragments, e.g. oligonucleotides up to 30 nucleotides, the hybridization temperature is below 65° C., for example at 50° C., preferably above 55° C., but below 65° C. Stringent hybridization temperatures are dependent on the size or length, respectively of the nucleic acid and their nucleic acid composition and will be experimentally determined by the skilled artisan. Moderately stringent hybridization temperatures are for example 42° C. and washing conditions with 0.2×SSC/0.1% SDS at 42° C.

Also contemplated herein are amino acid sequences of the above identified kind, which also encompass all sequences differing from the herein disclosed sequences by amino acid insertions, deletions, and substitutions.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity. This does not require more than routine experiments for the skilled artisan.

According to a further embodiment, the isolated nucleic acid of the invention further comprises a nucleic acid specifying one or more regulatory sequences operably linked thereto.

In a further embodiment, the present invention includes a vector comprising a nucleic acid. This vector is preferably an expression vector which contains a nucleic acid according to the invention and one or more regulatory nucleic acid sequences.

Numerous vectors are known to be appropriate for the transformation of bacterial cells, for example plasmids and bacteriophages, like the phage X, are frequently used as vectors for bacterial hosts. Viral vectors can be used in mammalian and insect cells to express exogenous DNA fragments, e.g. SV 40 and polyoma virus.

The transformation of the host cell can be done alternatively directly using "naked DNA" without the use of a vector.

The antibody/antibody fragment according to the invention can be produced either in eukaryotic or prokaryotic cells. Examples for eukaryotic cells include mammalian, plant, insect and yeast cells. Appropriate prokaryotic cells include *Escherichia coli* and *Bacillus subtilis*.

Preferred mammalian host cells are CHO, COS, HeLa, 293T, HEH or BHK cells or adult or embryonic stem cells.

Alternatively, the antibody/antibody fragment according to the invention can be produced in transgenic plants (e.g. potatoes, tobacco) or in transgenic animals, for example in transgenic goats or sheep.

According to a preferred embodiment, the vector is a plasmid or viral such as an engineered retrovirus or adeno virus.

According to a third aspect, the invention provides a pharmaceutical composition comprising an active component, preferably an antibody, a nucleic acid or a vector as defined hereinabove.

The active components of the present invention are preferably used in such a pharmaceutical composition in doses mixed with a pharmaceutically acceptable carrier or carrier material, that the disease can be treated or at least alleviated. Such a composition can (in addition to the active component and the carrier) include filling material, salts, buffer, stabilizers, solubilizers and other materials, which are known state of the art.

The term "pharmaceutically acceptable" is defined as non-toxic material, which does not interfere with effectiveness of the biological activity of the active component. The choice of the carrier is dependent on the application.

The pharmaceutical composition can contain additional components which enhance the activity of the active component or which supplement the treatment. Such additional components and/or factors can be part of the pharmaceutical composition to achieve a synergistic or additional effects or to minimize adverse or unwanted effects.

Thus, the pharmaceutical composition of the invention may further contain one or more pharmaceutically active ingredients in order to supplement the treatment.

Preferably, such pharmaceutically active ingredients are selected from antibiotic agents, antiinflammatory agents, and/or agents blocking further pattern recognition receptors. Those agents preferably are specific for CD14, LBP, MD-2, TLR3, TLR4, TLR5, TLR7, TLR8, and/or TLR9.

Techniques for the formulation or preparation and application/medication of compositions of the present invention are published in "Remington's Pharmaceutical Sciences", Mack Publishing Co., Easton, Pa., latest edition. A therapeutically effective dose relates to the amount of a compound which is sufficient to improve the symptoms, for example a treatment, healing, prevention or improvement of such conditions. An appropriate application can include for example oral, dermal, rectal, transmucosal or intestinal application and parenteral application, including intramuscular, subcutaneous, intramedular injections as well as intrathecal, direct intraventricular, intravenous, intraperitoneal or intranasal injections. The intravenous injection is the preferred treatment of a patient.

A typical composition for an intravenous infusion can be produced such that it contains 250 ml sterile Ringer solution and for example 1000 mg of the antibody of the invention. See also Remington's Pharmaceutical Science (15. edition, Mack Publishing Company, Easton, Ps., 1980).

The active component or mixture of it in the present case can be used for prophylactic and/or therapeutic treatments.

An amount which is adequate to reach the aforesaid effect is defined as "therapeutically effective dose". Amounts, which are effective for these applications, depend on the severity of the condition and the general condition of the patient. However, the dose range is usually between 1 and 100 mg antibody per kilogram body weight of the patient in need of the treatment. Systemic application of a specific antibody of the invention, i.e. T2.5 (see experimental part) upon lipopeptide challenge inhibited inflammatory mediator release such as TNFalpha and prevented lethal shock-like syndrome in mice. 20 mg/kg of T2.5 was sufficient to protect mice and administration of 40 mg/kg of T2.5 was protective even 3 h after start of otherwise lethal challenge with *Bacillus subtilis*. Therefore, for treating mammals a dose of between 10 to 60 mg and more preferably between 20 to 40 mg per kilogram body weight is appropriate. Single or multiple applications after a daily, weekly or monthly treatment regimen can be performed with application rate and samples chosen by the physician in charge. These applications largely depend from the question, whether a chronic or acute condition is to be prevented or treated. An individual dose is administered as a single dose to the mammal suffering from an acute infection, wherein the individual dose is administered repeatedly to a mammal suffering from a chronic infection and/or inflammation.

The invention is additionally directed to a hybridoma which produces a monoclonal antibody as defined herein.

The antibody, nucleic acid, vector or composition of the present invention preferably are used in the prevention and/or treatment of inflammatory processes or any other process induced by bacterial infection, trauma, or chronic inflammation. Furthermore, they can be used for the prevention and/or treatment of bacteriaemia or sepsis. The chronic infection preferably is selected from rheumatoid or vascular arthritis or inflammatory bowel disease.

The present invention in particular is directed to a gene therapy approach for use in the treatment of chronic diseases. The approach basically follows the already known protocols for gene therapy and comprises in particular the step of cloning a sequence comprising the variable domains of the antibody of the invention as specified above into an expression vector and introducing said expression vector into a host, for example a human patient in order to cause an overexpression of said antibody/antibody fragment in said patient.

According to a fourth aspect, the present invention is further directed to a screening method for identifying an antagonist capable of inhibiting or blocking TLR2, comprising the steps of:
(a) generating or providing mammalian TLR2,
(b) contacting said TLR2 with a candidate compound,
(c) detecting the inhibition or blocking of said compound by a suitable detection method,
(d) selecting a compound that has been tested positive in step (c),
(e) optionally repeating steps (a)-(d) with a suitably modified form of the compound of step (d).

The present invention is in additionally directed to the following embodiments:
1. An antagonist, which specifically inhibits or blocks the mammalian, preferably human, Toll-like receptor 2 (TLR2).
2. The antagonist of emb. 1, which is an antibody, small molecule or an aptamer.
3. The antibody of emb. 2, which is a polyclonal antibody, a monoclonal antibody, a humanized antibody, a chimeric antibody, or a synthetic antibody.
4. The antibody of emb. 3, which is directed against the extracellular domain of TLR2.

5. The use of an antagonist of one or more of emb. 1-4 in the prevention and/or treatment of acute and/or chronic inflammatory processes induced by bacterial infection.
6. A screening method for identifying an antagonist capable of inhibiting or blocking TLR2, comprising the steps of:
    (f) generating or providing mammalian TLR2,
    (g) contacting said TLR2 with a candidate antagonist,
    (h) detecting the inhibition or blocking of said candidate antagonist by a suitable detection method,
    (i) selecting a candidate antagonist that has been tested positive in step (c),
    (j) optionally repeating steps (a)-(d) with a suitably modified form of the candidate antagonist of step (d).

The present invention will be further described with reference to the following figures and examples; however, it is to be understood that the present invention is not limited to such figures and examples.

Figure 1:
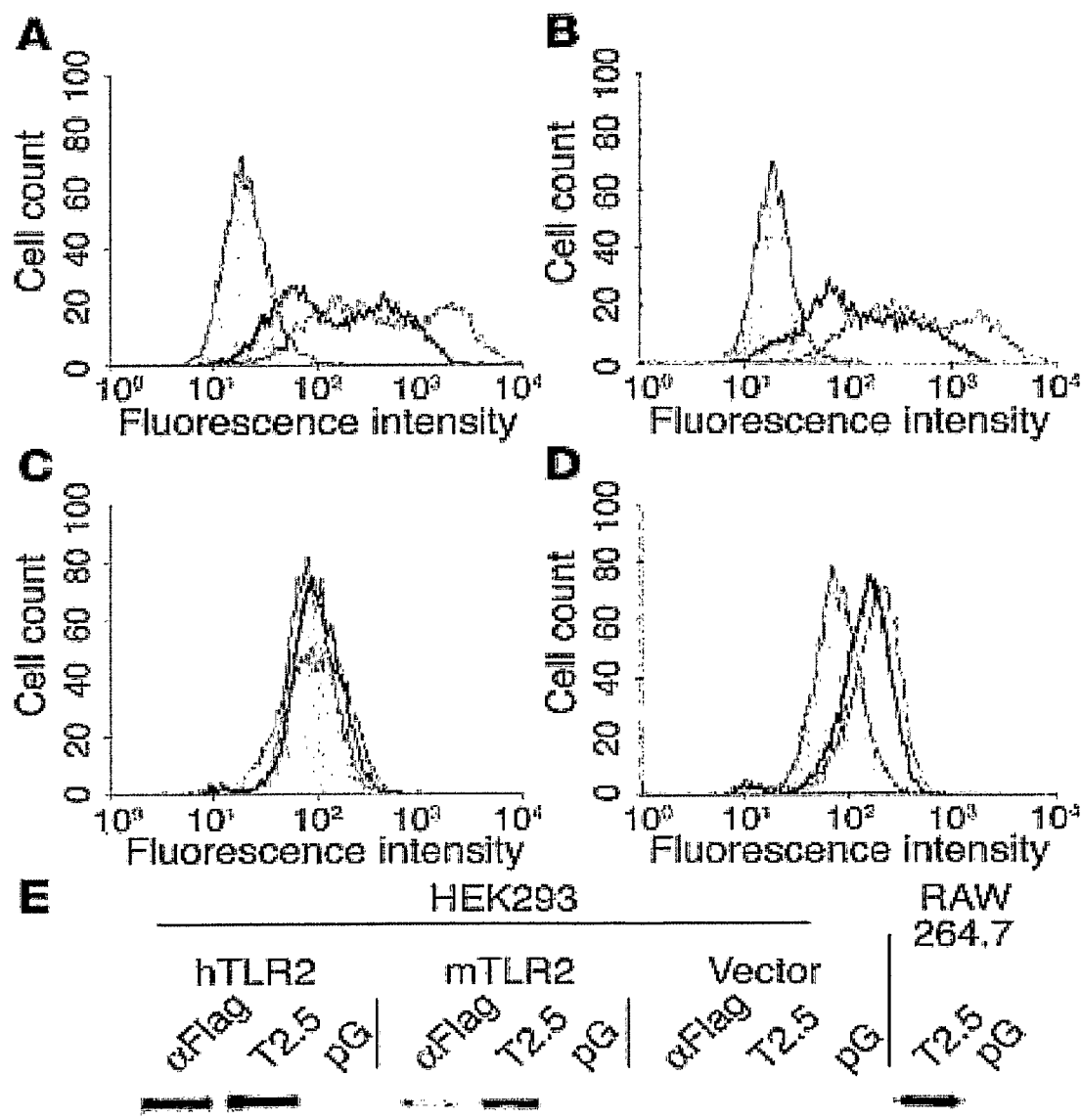

FIG. 1 Application of mAb T2.5 for specific detection of TLR2. Results of flow-cytometry of HEK293 cells stably overexpressing Flag-tagged mTLR2 (a) or human TLR2 (b), as well as primary TLR2$^{-/-}$ (c) and wild-type murine macrophages (d) by staining with mAb T2.5 (bold line, unfilled area). Negative controls represent cells not stained with a primary, but incubated with a mouse IgG specific secondary antibody (filled areas). For positive controls, Flag-(a and b) and mTLR2 (c and d) specific polyclonal antisera were used (normal line, unfilled area). For immunoprecipitation with T2.5, lysates of HEK293 cells overexpressing murine or human TLR2, as well as of murine RAW264.7 macrophages were applied as indicated (e). TLR2 precipitates were visualized by application of Flag (HEK293) or mTLR2 (RAW264.7) specific polyclonal antisera. Flag specific (αFlag) and protein G beads in the absence of antibodies (pG), as well as vector transfected HEK293 cells were used as controls. The size of TLR2 was 97 kDa.

FIG. 2 Subcellular localization of TLR2 in vitro. MAb T2.5 was used for cytochemical detection of overexpressed murine and human TLR2 (a), as well as endogenous murine (TLR2$^{+/+}$, wild-type) or human TLR2 in primary macrophages (b). Vector transfected HEK293 cells, as well as TLR2$^{-/-}$ primary macrophages were analyzed as staining controls. Concanavalin A was used for staining of cytoplasmic membranes. The bars in the lower right corners of each field represent a distance of 20 μm (a) or 10 μm (b) on the slides analyzed.

FIG. 3 Inhibitory effect of mAb T2.5 on cell activation in vitro. NF-κB dependent luciferase activities in HEK293 cells overexpressing either murine (a) or human TLR2 (b), as well as TNFα concentrations in supernatants of RAW264.7 (c) or primary murine macrophages (d) challenged with inflammatory stimulants are shown (ND, not detectable). Cells were incubated either with T2.5 or conT2 only (empty bars), or additionally challenged with IL-1β (a, b, horizontally hatched bars), ultra pure LPS (c, d, bold upward hatched bars), P$_3$CSK$_4$ (filled bars), or h. i. B. subtilis (downward hatched bars, a to d). MAb and challenge (P$_3$CSK$_4$, LPS) dependent NF-κB/p65 nuclear translocation in human macrophages (e) was analyzed by cytochemical staining (Unstim., unstimulated). NF-κB dependent electro mobility shift assay (EMSA) and phosphorylation of MAP kinases Erk1/2 (pErk1/2) and p38 (pP38), as well as Akt (pAkt) were analyzed by applying nuclear or total extracts, respectively, from RAW624.7 macrophages (f, g). Cells were preincubated with the amounts of mAb T2.5 or conT2 indicated (μg/ml) and subsequently challenged with P$_3$CSK$_4$ or LPS for 90 min (f, arrows indicate specific NF-κB-DNA complexes) or 30 min (g, P38, specific immunoblot as positive control). Untreated cells (control) were analyzed as controls.

Figure 4:
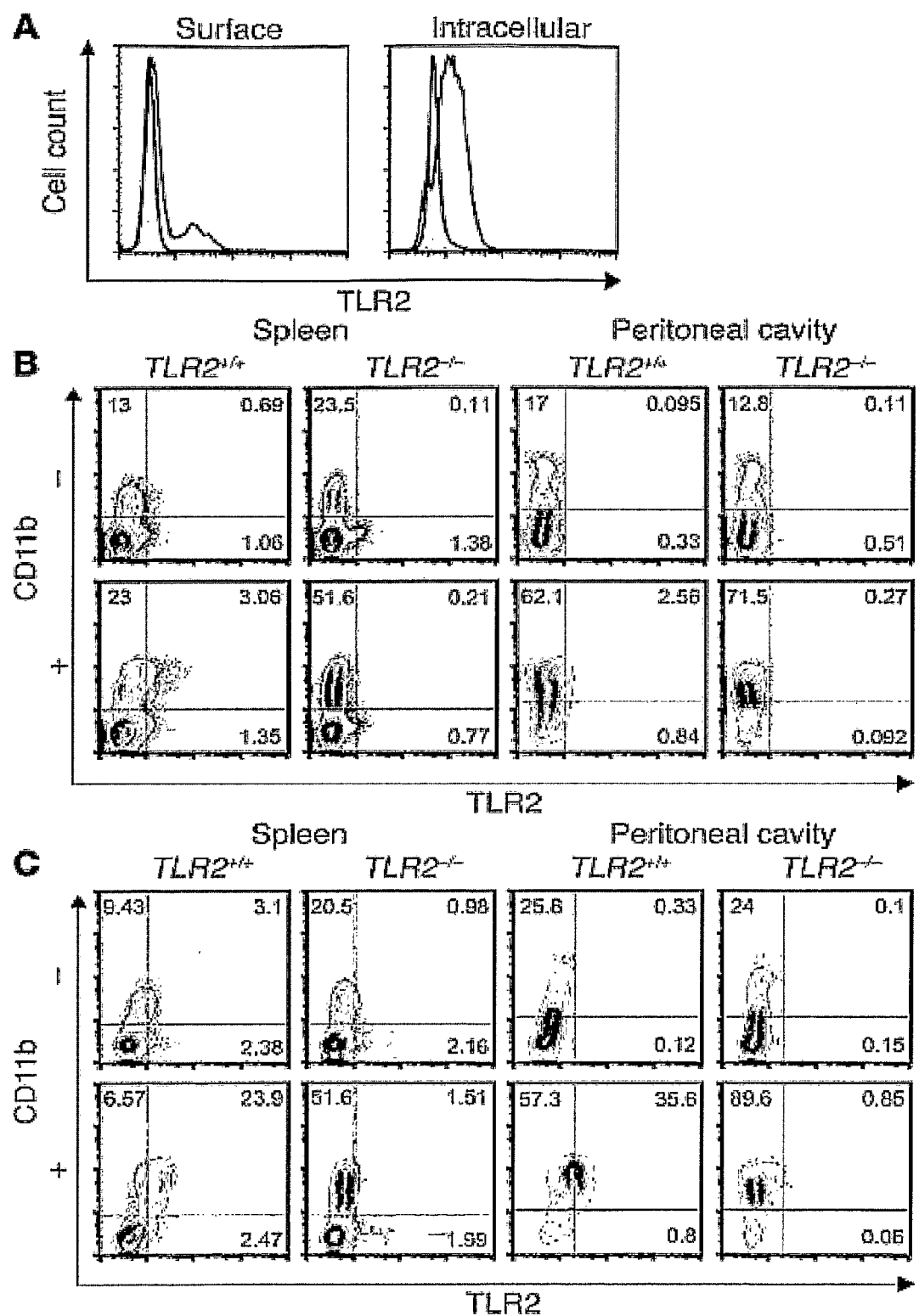

FIG. 4 TLR2 expression in vivo. Flow-cytometry of splenocytes and peritoneal washout cells from wild-type and TLR2$^{-/-}$ mice ex vivo immediately upon isolation (n=5, cells pooled for each sample). CD11b$^+$ splenocytes from mice challenged with LPS for 24 h were analyzed for surface and intracellular TLR2 expression (a) by staining with T2.5 (bold line, TLR2$^{+/+}$; filled area, TLR2$^{-/-}$). For analysis of TLR2 regulation upon infection (b, c), mice were either left uninfected (−) or infected with Gram-positive B. subtilis and sacrificed after 24 h (+). Upon staining of CD11b, cells were stained with T2.5 (TLR2) either without (b) or upon permeabilization (c). Numbers in quadrants represent the proportion of single or double stained cells, respectively, as compared to the total number of viable cells analyzed (%).

Figure 5:
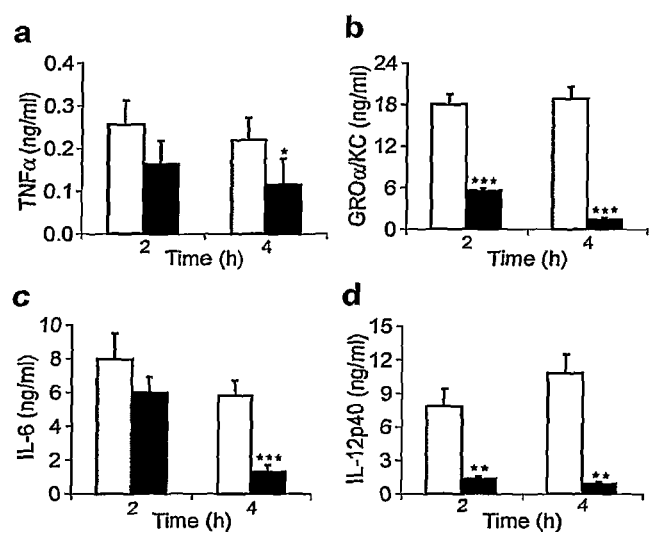

FIG. 5 Inhibitory effect of mAb T2.5 on host activation by microbial challenge in vivo. Mice were pretreated i. p. with 1 mg mAb T2.5 (solid bars) or left untreated (empty bars). Mice were challenged after 1 h with P$_3$CSK$_4$ and D-galactosamine (i. p.), as well as sacrificed 2 h or 4 h later (n=4 for each group at each time point). Serum concentrations of TNFα (a), GROα/KC (human IL-8 homologue) (b), IL-6 (c), and IL-12p40 (d) were analyzed by ELISA (*p<0.05, p<0.005, *p<0.001, student's t-test for unconnected samples).

Figure 6:
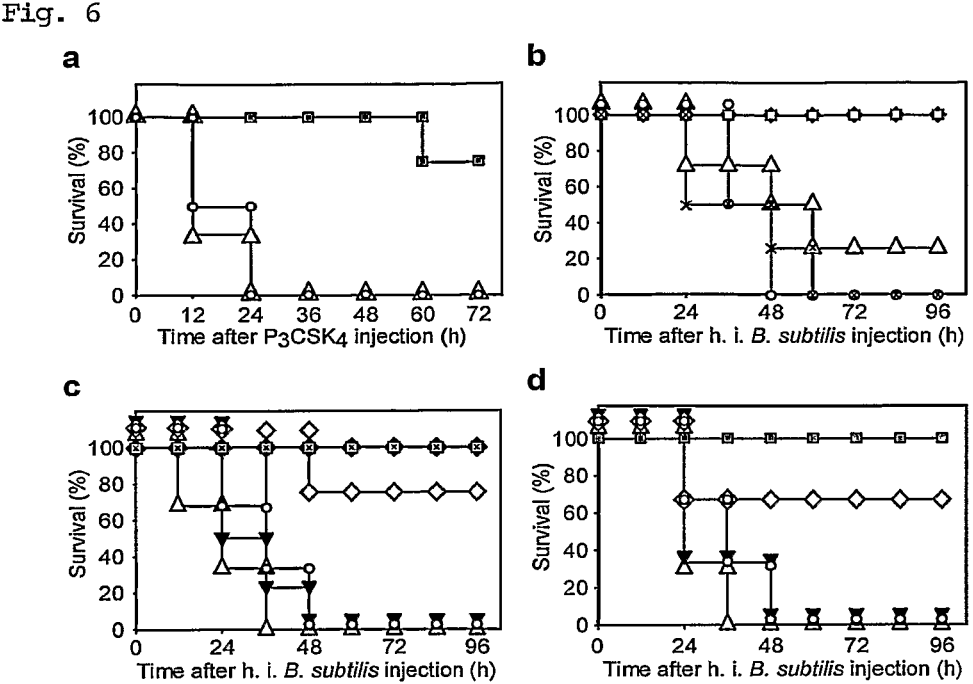

FIG. 6 Effects of mAb T2.5 administration on viability upon TLR2-specific systemic challenging. IFNγ and D-galactosamine sensitized mice received either no mAb, 1 mg of mAb T2.5, or 1 mg of conT.2 i. p. 30 min prior to microbial challenge with bacterial lipopeptide analogue P$_3$CSK$_4$ (a, open circles, no mAb, n=4; open triangles, mAb conT2, n=3; filled squares, mAb T2.5, n=4). Mice challenged with a high dose of h. i. B. subtilis were left untreated or treated 1 h later with dosages of mAb T2.5 indicated (b, filled diamonds, 1 mg, n=3; open squares, 0.5 mg, n=3; open triangles, 0.25 mg, n=4; x's, 0.13 mg, n=4; open circles, no mAb T2.5, n=4) or with 1 mg of Abs as indicated at different time points (c, d). Administration of TLR2-specific mAb prior (−), as well as after (+) bacterial challenge (c, filled inverted triangles, no mAb, n=8; open circles, mAb conT2, −1 h, n=3; filled diamonds, mAb T2.5, −1 h, n=4; open squares, mAb T2.5, +1 h, n=3; x's, mAb T2.5, +2 h, n=3; open diamonds, mAb T2.5, +3 h, n=4; open triangles, mAb T2.5, +4 h, n=3). Administration of TLR2-specific mAb T2.5 prior (−) to bacterial challenge (d, n=3 for experimental groups: open triangles, no mAb; filled squares, mAb T2.5, −3 h; open diamonds, mAb T2.5, −4 h; open circles, mAb T2.5, −5 h; filled inverted triangles, mAb T2.5, −6 h).

Figure 7:
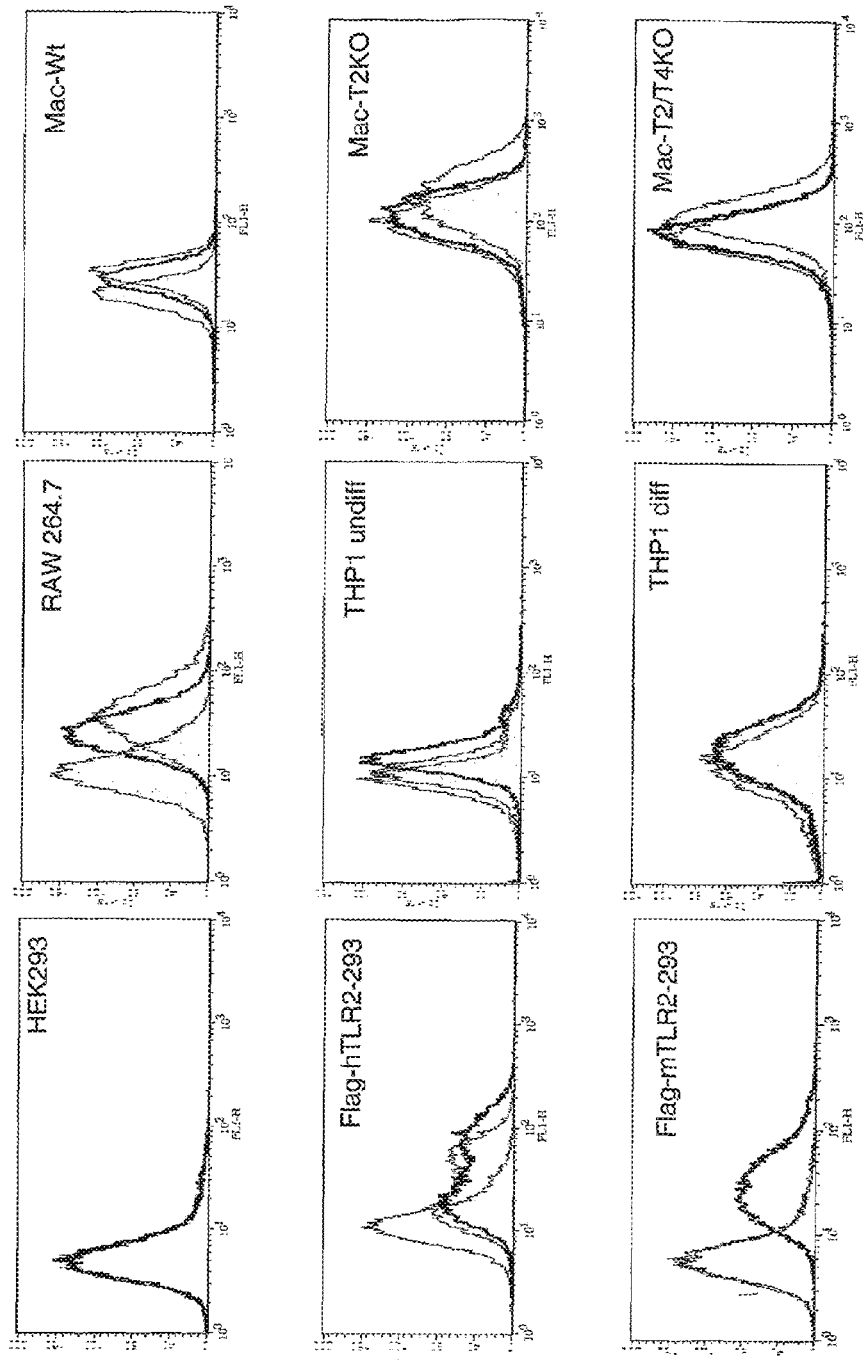

FIG. 7 depicts a FACS analysis demonstrating that T2.5 specifically recognizes both murine and human TLR2, while TL2.1 interacts with human TLR2 and an unspecific antigen from murine cells. FACS was performed using 5% NGS and 1% Fcblock as blocking agents, with 5 μg/ml primary antibody (TLR2.1 and T2.5), and 3.5 μg/ml FITCGoat anti-mouse IgG (Fab) as secondary antibody.

Figure 8:
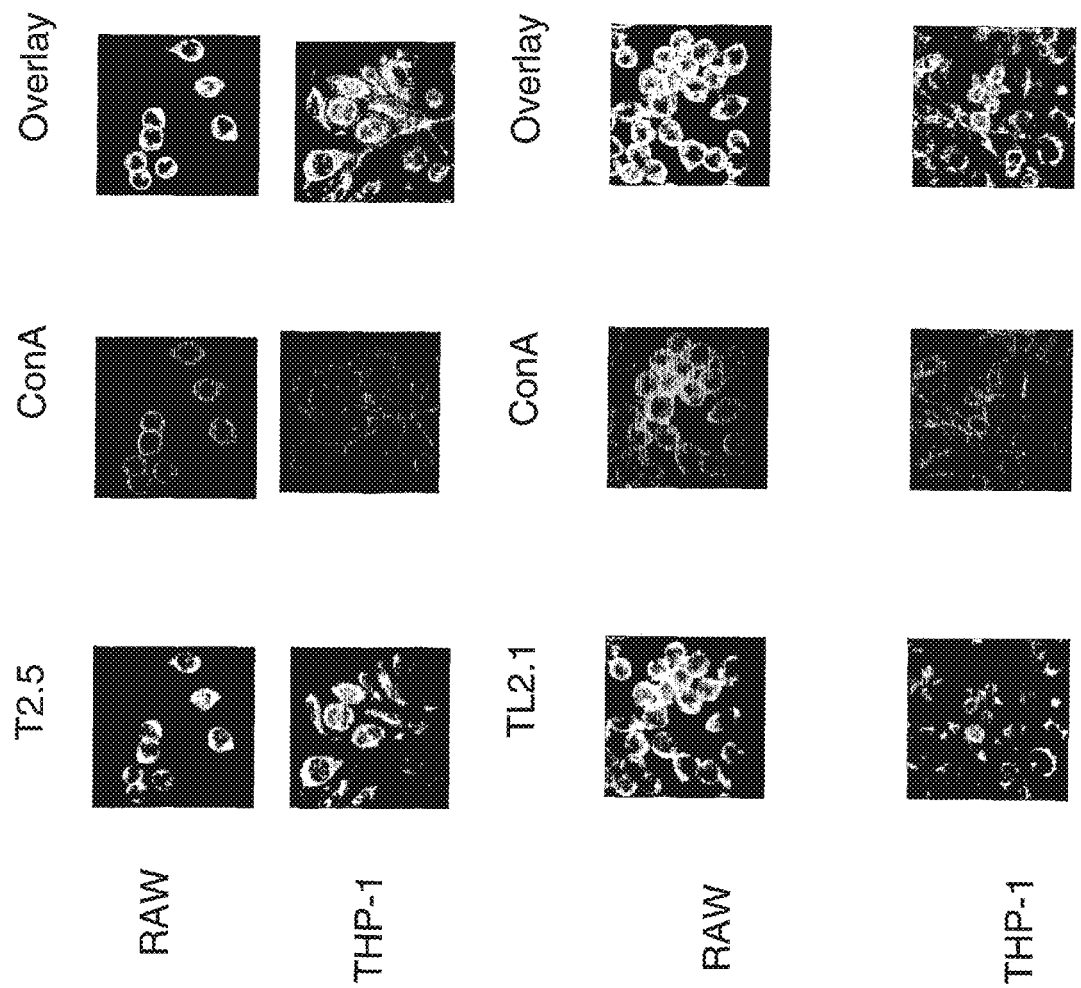
Figure 9:
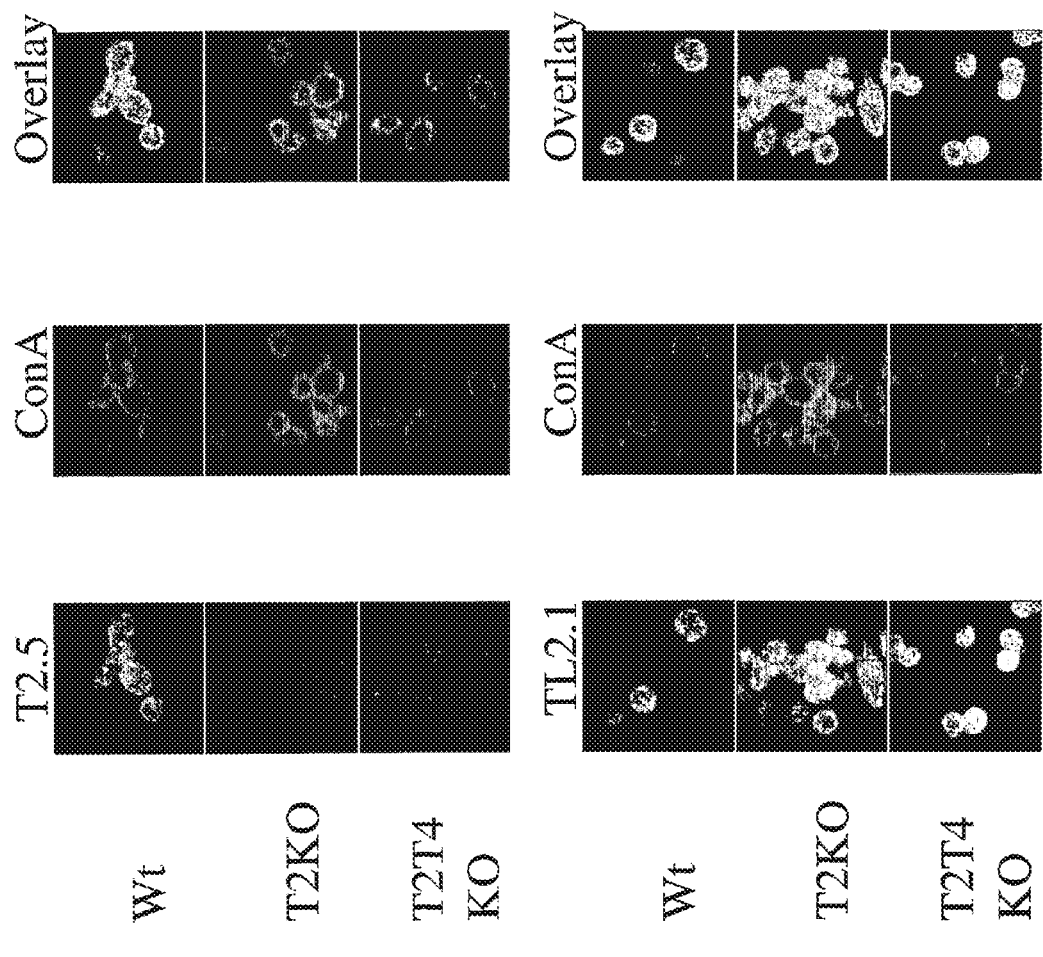

FIGS. 8 and 9 depict immunocytochemistry experiments demonstrating that T2.5 specifically recognizes both murine and human TLR2, while TL2.1 interacts with human TLR2 and a nonspecific antigen from murine cells in 1HC analysis. Immunocytochemistry was performed as follows:
1. Seed 1×10$^5$ Cells/cover glass/ml/well on 24-well plate, culture overnight.
2. Fix cells with Methanol at −20 degree for 8 minutes.
3. Wash with PBS for 3 times (dip into 3 beakers containing PBS).

4. Block with 2% NGS (normal goat serum in PBS) at 37 degree for 20 minutes in a humid chamber (20-30 μl for each slide).
5. Incubate with T2.5/TL2.1 (5 μg/ml) in 2% NGS at 37 degree for 60 minutes in a humid chamber (20-30 μl for each slide).
6. Wash with PBS for 3 times (dip into 3 beakers containing PBS).
7. Incubate with secondary antibody (AlexaFluoro546 conjugated goat anti mouse IgG, cat, A-11030, 8 μg/ml, Molecular Probes, Leiden, Netherlands) in 2% NGS at 37 degree for 60 minutes in a humid chamber (20-30 μl for each slide).

Option: Incubate with AlexaFluoro488 conjugated Concanavalin A for cell surface staining (AlexaFluoro488 conjugated Concanavalin A, cat. C-11252, 25 μg/ml, Molecular Probes, Leiden, Netherlands) in 2% NGS at 37 degree for 60 minutes in a humid chamber together with secondary antibody (20-30 μl for each slide).
8. Wash with PBS for 3 times (dip into 3 beakers containing PBS).
9. Dry at RT for 20 minutes in dark, mount in mounting reagent, observe with confocol microscope (LSM510, Carl Zeiss, Oberkochen, Germany).

Figure 10:
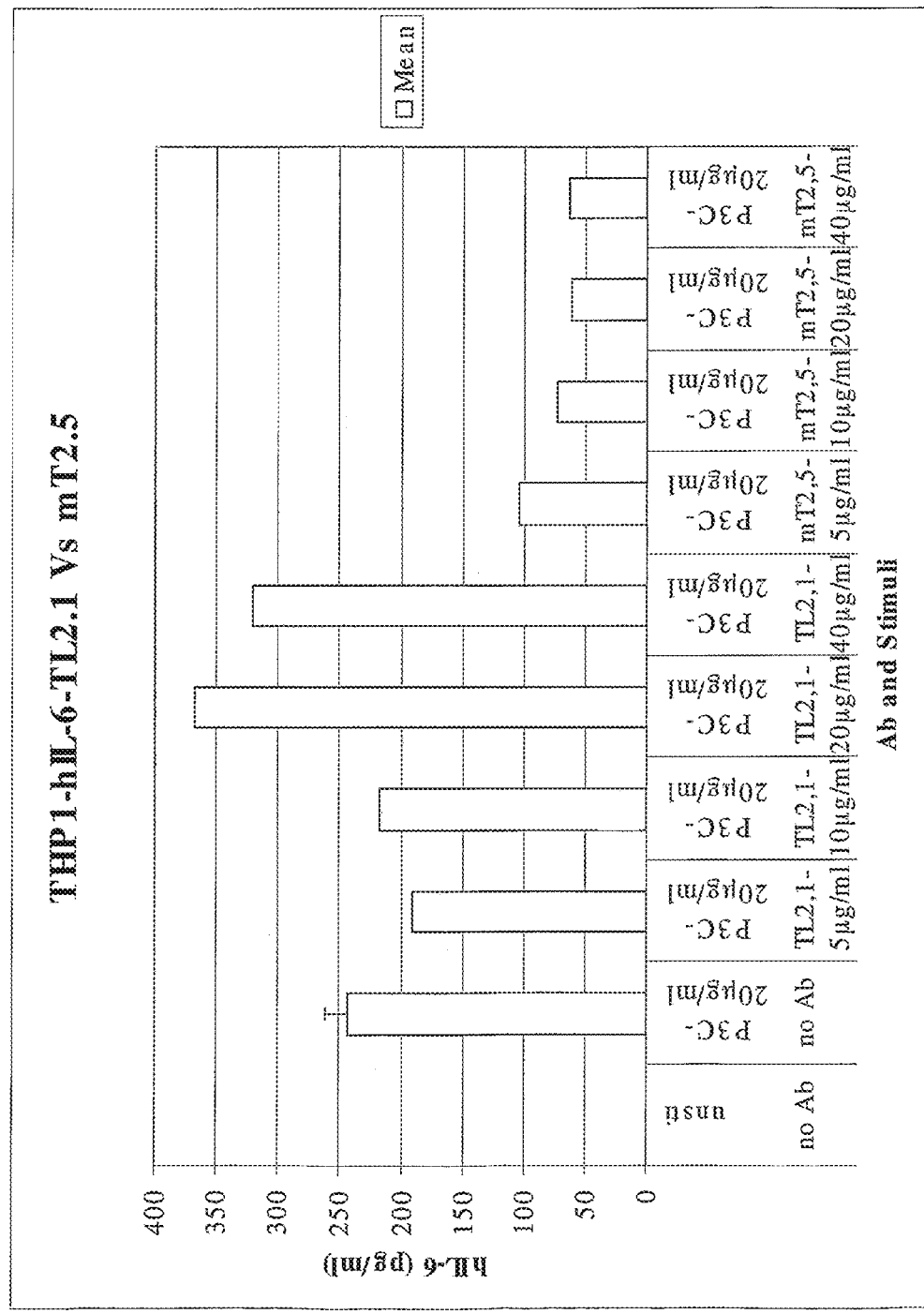
Figure 11:
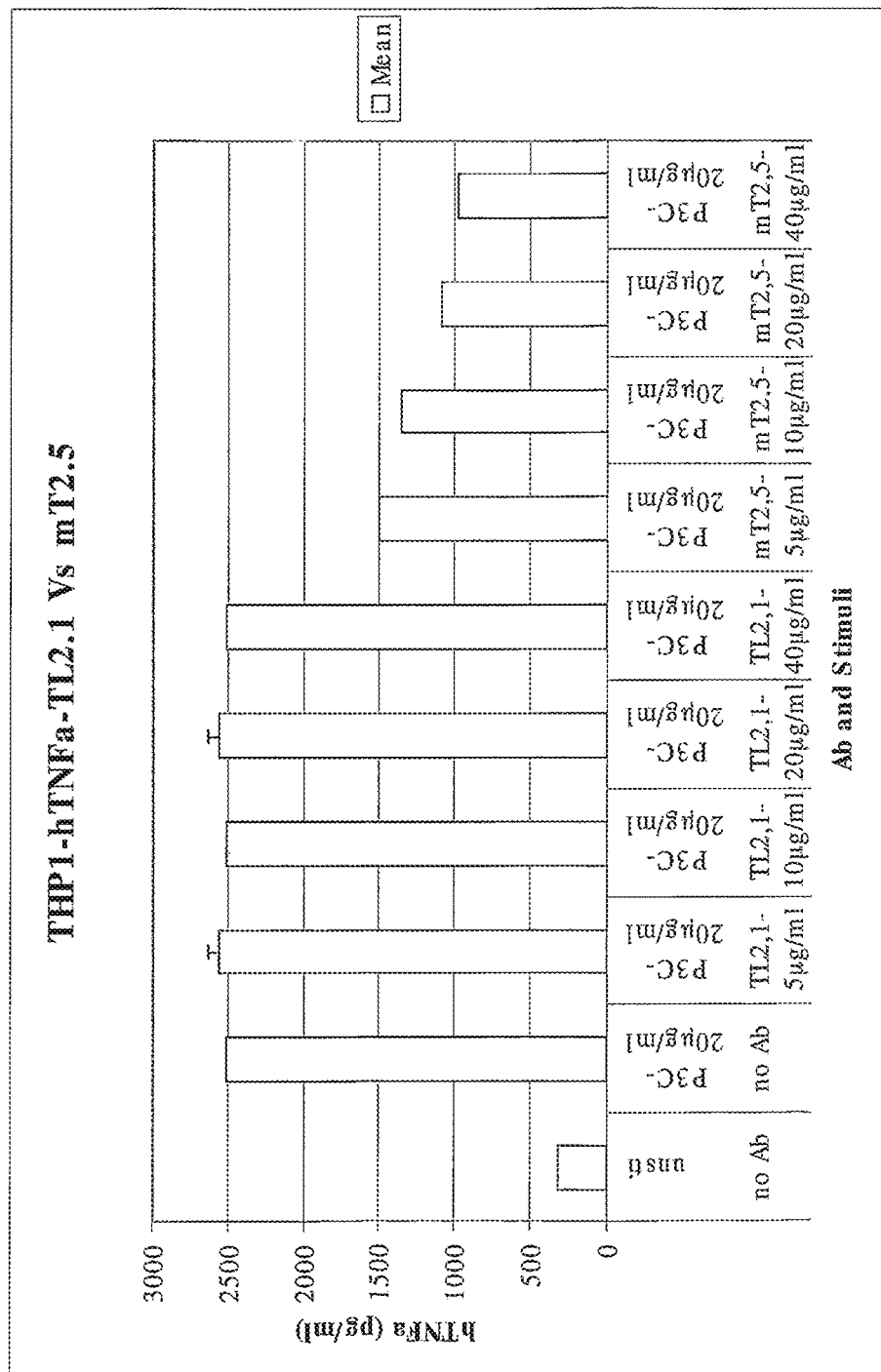
Figure 12:
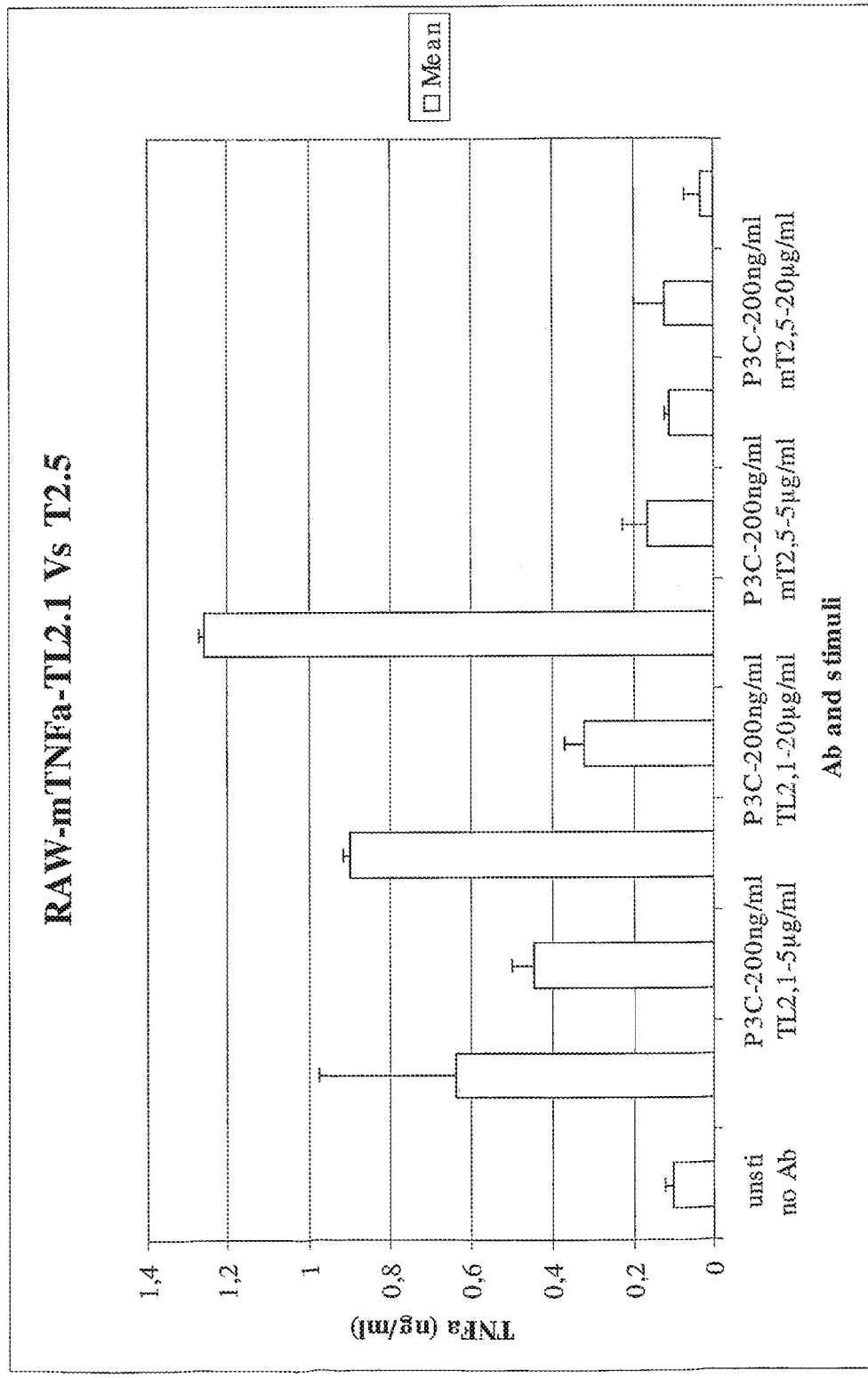

FIGS. 10 to 12 Dose dependent inhibition of cell activation by T2.5 but not by TL2.1 in both THP1 and RAW cells.

In order to analyze potential TLR2-inhibitory difference of TL2.1 and T2.5, human THP1 and murine RAW264.7 cells were used. Doses of both TL2.1 and T2.5 ranging from 5 μg/ml to 40 μg/ml as indicated in the figure were applied 30 min prior to challenge with $P_3CSK_4$ at indicated concentrations. TNFα and IL-6 concentrations in supernatants of THP1 and RAW264.7 cells were analyzed 24 h after start of challenge.

Figure 13:
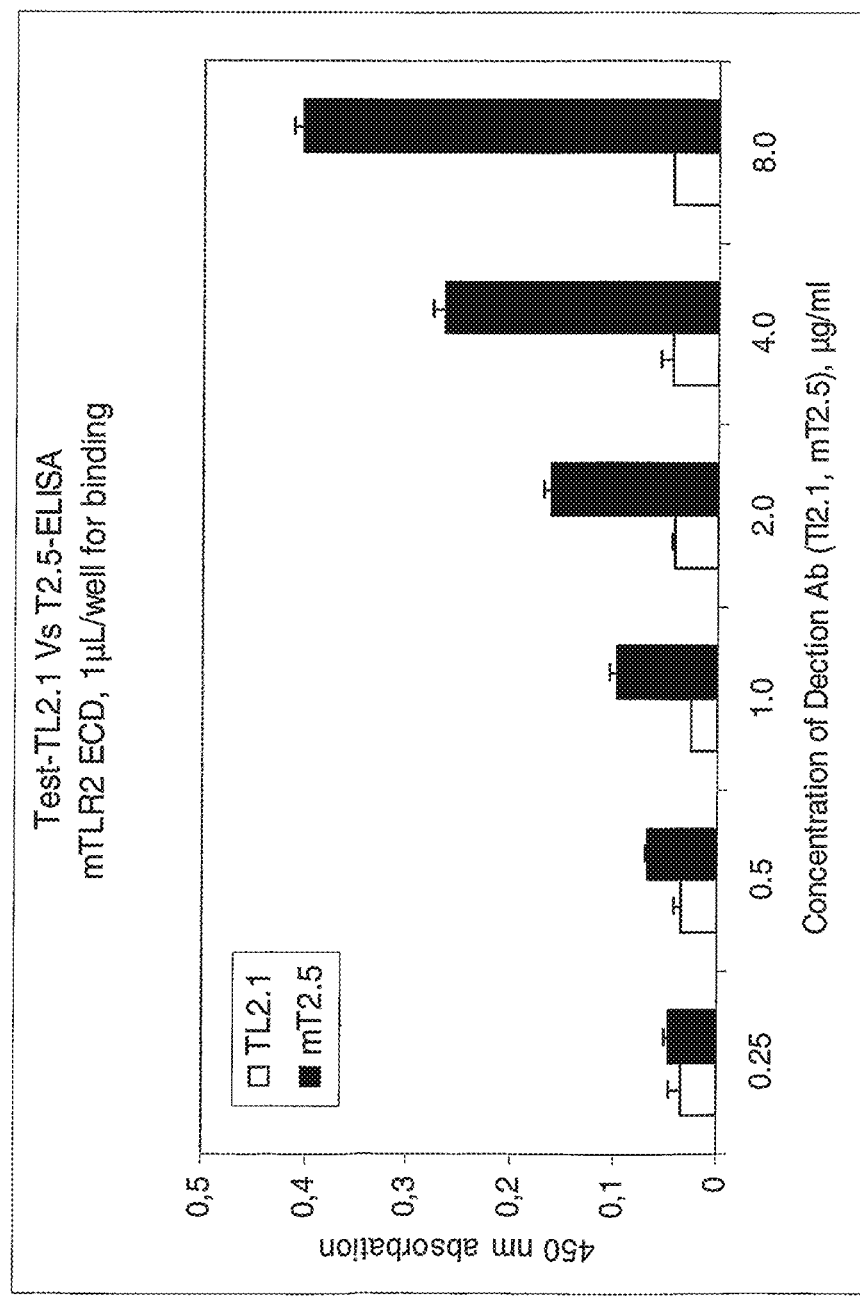

FIG. 13 Dose dependent binding of T2.5 to mTLR2ECD versus failed binding of TL2.1 to the same antigen in ELISA.

ELISA plates were coated with anti human IgG Fc antibody, human IgGFc fused mouse TLR2ECD protein was then immobilized after BSA blocking and washing followed by detection with T2.5 and TL2.1 at various concentrations as indicated. Specific signals were visualized via application of HRP conjugated anti mouse IgG after primary antibody incubation followed by reaction with HRP substrates.

Figure 14:
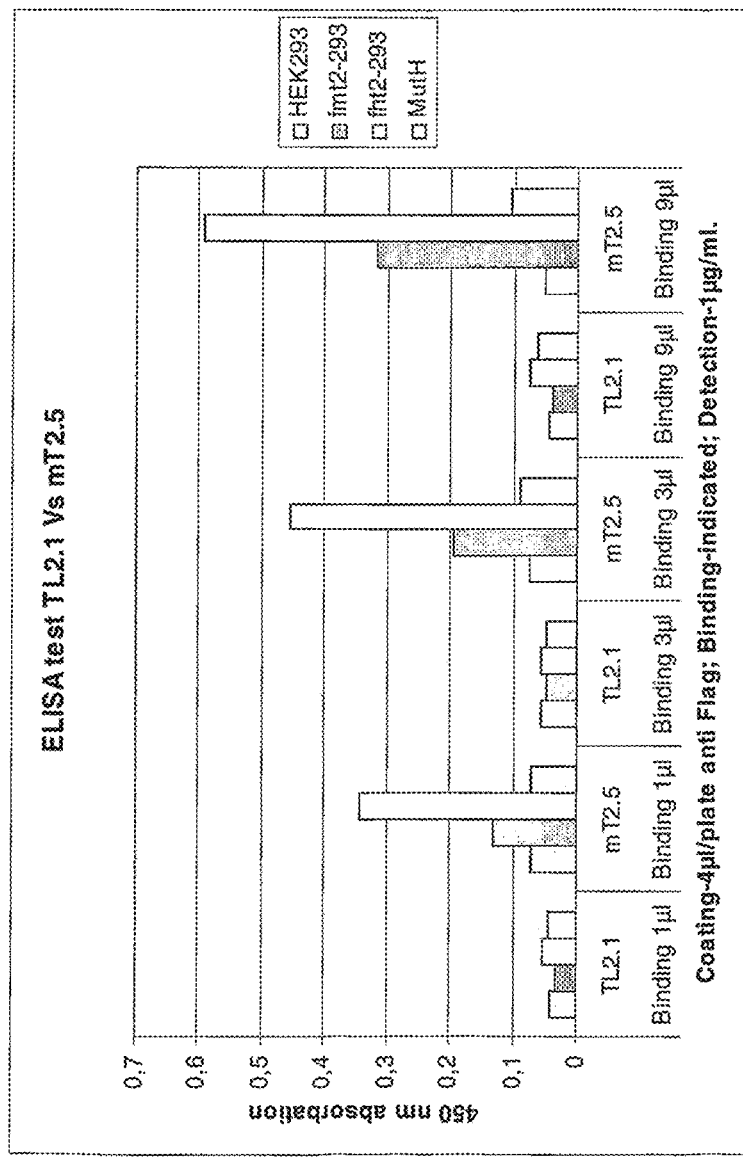

FIG. 14 TL2.1 lacks binding capacity to overexpressed murine and human TLR2 in ELISA while T2.5 binds both in the same assay.

ELISA plates were coated with anti Flag antibody, Flag fused mouse and human TLR2 and control proteins were then immobilized after BSA blocking and washing followed by detection with T2.5 and TL2.1 at 1 μg/ml as indicated. Specific signals were visualized via application of HRP conjugated anti mouse IgG after primary antibody incubation followed by reaction with HRP substrates.

Figure 15:
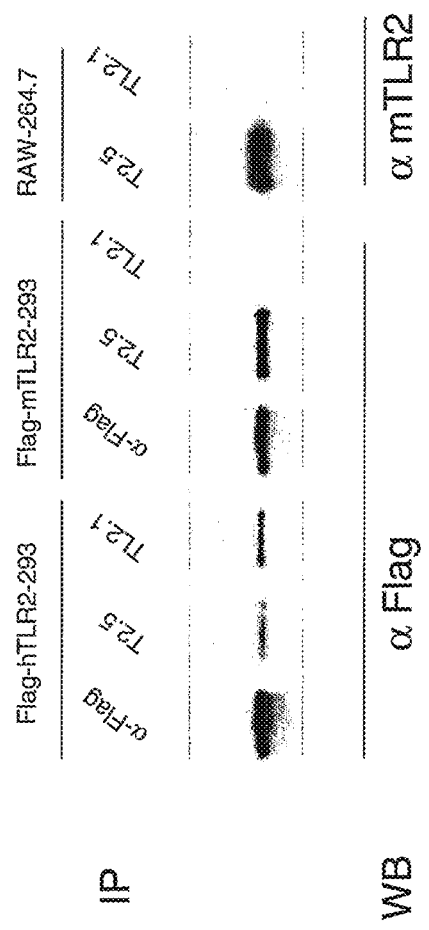

FIG. 15 Lack of interaction between TL2.1 and murine TLR2 in Immunoprecipitation and subsequent immunoblot analysis.

Lysates of $1\times10^6$ murine RAW264.7 macrophages or HEK293 cells, 1 μg of each antibody as indicated, and 20 μl of protein G beads (Santa Cruz, Calif., USA) were mixed for o. n. precipitation. Immune complexes were analyzed by immunoblot analysis with either Flag- or murine TLR2-specific antiserum.

FIG. 16: Antibodies (Abs) for immunoprecipitation (IP), as indicated, hT2.5 stands for linearized T2.5 heavy chain and light chain fused with C terminal human IgG1 Fc. Antigens (Ags) for IP: for lanes 1, 3, 5, 7, 9, lysates from HEK 293 cells overexpressing Flag-tagged mouse TLR2, for lanes 2, 4, 6, 8, 10, lysates from HEK293 cells without any transfection. A Western Blot (WB) was done with anti-Flag polyclonal sera. Binds at 97 kD resolved on 10% SDS-PAGE gel indicate the position of Flag tagged murine TLR2 upon overexpression in HEK 293 cells precipitated with Abs.

FIG. 16A1-3:

A single chain (FIG. 16A1) and partially humanized TLR2-specific (hT2.5, FIG. 16A3) antibody was generated by subcloning of a mammalian expression construct in the vector pcDNA3.1 within which expression is driven by the CMV promoter (FIG. 16A2). From the 5' end of the MCS sequence encoding a portion of the variable heavy chain (base residue 1 to 450, see SEQ ID NO: 1), was followed successively by a linker sequence encoding 15 amino acids (Gly and Ser), a sequence encoding a portion of the variable light chain (base residue 61 to 396, see SEQ ID NO: 2), as well as the cds of the human Fcg (gamma) chain forming the 3' terminus (C terminus of the expressed hT2.5 protein) of the construct.

FIG. 17:

Molecular analysis of mAb T2.5 effects on TLR2ECD-$P_3CSK_4$ interaction. Binding of recombinant TLR2ECD-Fc fusion protein (T2EC, positive controls) to immobilized $P_3CSK_4$ upon pre-incubation with T2.5 (T2EC+T2.5) at different molar excesses (a, ×1, ×3.3, ×10) or with an isotype matched control mAb (T2EC+con) at 10 fold molar excess only (b, ×10). Binding was continuously monitored in a SPR biosensor device and amounts of antibodies used to gain high molecular excess over T2EC (co-incubation) were applied alone as negative controls (a, T2.5; b, con). Response units (RU) at 300 s are a measure for $P_3CSK_4$-binding capacities of T2EC and T2EC+mAb. For analysis of approximate localization of T2.5 epitope within the TLR2ECD, a mutant human TLR2 construct lacking the N-terminal third of the LRR-rich ECD domain (hTLR2-mutH) was used for NF-κB dependent luciferase assay upon transient transfection, preincubation with mAb (T2.5, conT2), and $P_3CSK_4$ challenge (c, solid bars). Absence of mAb treatment (no mAb) and/or $P_3CSK_4$ challenge (empty bars), as well as empty vector (Vector) represent respective controls (c).

FIG. 18:

Inhibitory effect of recombinant single chain and partially humanized hT2.5 antibody on lipopeptide induced cell activation. HT2.5 was overexpressed in HEK293 cells and supernatant collected (see. FIG. 16). HEK293 cells were either transfected with reporter plasmids only (open bars) or cotransfected with human TLR2 (black bars). Three groups of samples were established for both TLR2" and TLR2$^+$ cells as indicated. To samples of the first group, regular supernatant of normal HEK293 cells was administered. In the second group, cells were pretreated with culture supernatants of HEK293 cells overexpressing hT2.5. As positive control, application of 50 μg/ml of T2.5 to supernatants in group three was performed. Specifically, cells of the groups one and two were pretreated by four times removal of supernatant and subsequent addition of conditioned supernatant for 10 min each time while group three samples were treated by a single application of T2.5 to the original supernatants. One set of all samples was left untreated while a second set of samples was treated by application of lipopeptide analogue (P3CSK4) at a concentration of 100 ng/ml 40 minutes after antibody (T2.5 or hT2.5) incubation. NF-κB dependent reportergene activation was analyzed 6 h upon start of lipopeptide challenge.

Result: The inhibitory effect of recombinant hT2.5 was similar to that of native T2.5 on TLR2-dependent cell activation.

Abbreviations used herein: TLR, Toll-like receptor; mAb, monoclonal antibody; $P_3CSK_4$, tripalmitoyl-cysteinyl-seryl-(lysyl)3-lysine; h. i. B. subtilis, heat inactivated Bacillus subtilis; sPGN, soluble peptidoglycan; LTA, lipoteichoic acid Examples Application of Murine mAb T2.5 for Expression Analysis In Vitro The inventors selected an IgG1κ anti TLR2 mAb named T2.5 which specifically recognized TLR2. HEK293 cells stably expressing murine or human TLR2 were stained specifically on their surface by T2.5 (FIGS. 1a and b). Furthermore, T2.5 did not bind to primary murine $TLR2^{-/-}$, but bound to wild-type macrophages cultured in vitro (FIGS. 1c and d). T2.5 immuno-precipitated native murine and human TLR2 from lysates of HEK293 cells overexpressing each of the two TLR2 orthologs (FIG. 1e). Most importantly, T2.5 precipitated endogenous TLR2 from lysates of RAW264.7 macrophages (FIG. 1e). Next, the inventors analyzed T2.5 for its capacity to specifically detect TLR2 on the subcellular level. Overexpressed murine and human TLR2 (FIG. 2a), as well as endogenous TLR2 were detectable in primary murine and CD14+ leukocyte derived human macrophages (FIG. 2b).

Inhibitory Effects of T2.5 on TLR2 Specific Cell Activation

T2.5 inhibited murine and human TLR2 mediated cell activation by TLR2 specific stimuli $P_3CSK_4$ or B. subtilis applied to HEK293 cells overexpressing TLR2, murine RAW264.7, and primary macrophages as measured by NF-κB dependent reporter gene assay and IL-8 specific enzyme linked immuno sorbent assay (ELISA), as well as TNFα and IL-6 specific ELISA, respectively (FIG. 3a to d and data not shown). A second newly generated IgG1κ anti TLR2 mAb, conT2, was used as a control. This mAb binds native murine (m) TLR2 in a manner comparable to T2.5 but not human TLR2 (data not shown) and failed to inhibit TLR2 dependent cell activation (FIG. 3). Also, no inhibition of 1'-1 receptor or TLR4 signaling by T2.5 was detected, indicating that TLR2 independent signaling pathways in T2.5 treated cells remain intact (FIG. 3a to d). Moreover, TLR2 mediated nuclear translocation of NF-κB was specifically inhibited by T2.5 in human macrophages (FIG. 3e). NF-κB specific electro mobility shift assay (EMSA), as well as anti phospho p38, Erk1/2, and Akt immunoblot analysis revealed T2.5 but not conT2 dose dependent inhibition of $P_3CSK_4$ induced NF-κB-DNA binding and cellular kinase phosphorylation (FIG. 3f and g).

Flow-Cytometry of Intracellular and Surface TLR2 Expression Ex Vivo

Since LPS induces TLR2 expression in primary macrophages in vitro (data not shown), the inventors first compared T2.5 specific staining of CD11b+ splenocytes from LPS challenged wild-type and $TLR2^{-/-}$ mice by flow-cytometry. Weak surface staining and pronounced intracellular staining were seen (FIG. 4a). In subsequent experiments, peritoneal cells and splenocytes from mice infected with the Gram-positive bacterium B. subtilis were analyzed. While surface expression of TLR2 in primary murine macrophages was relatively strong upon in vitro culture (FIG. 1d), surface expression was weak or not detectable in unchallenged CD11b+, CD11c+, CD19+, and GR1+ subpopulations of splenocytes and peritoneal washout cells (FIG. 4a, b and data not shown). Upon microbial challenge, however, TLR2 surface expression strongly increased in CD11b+ and GR1+ cells (FIG. 4b and data not shown). Signals were specific as tested by analysis of $TLR2^{-/-}$ cells (FIG. 4). Again, intracellular staining of TLR2 revealed significant levels of intracellular TLR2 expression which increased to a higher degree than surface expression upon microbial challenge (FIG. 4a and b).

Antibody Mediated Interference with TLR2 Specific Immune Responses Towards Systemic Challenge Next, the inventors determined cytokine and chemokine serum concentrations in mice, either pretreated, or not pretreated with T2.5, as well as challenged with $P_3CSK_4$. While cytokine and chemokine concentrations were low in sera of untreated mice (see methods), serum levels of TNFα, IL-8, IL-6, and IL-12p40 were significantly lower in mice preinjected with T2.5 as compared to controls and measured after challenge (FIG. 5a to d).

Both, a high dose (microbial product only) and a low dose model (additional sensitization with D-galactosamine) have been established for bacterial product induced shock in mice[26]. In order to interfere in a strictly defined model of septic shock, the inventors applied the bacterial lipopeptide analogue and TLR2 agonist $P_3CSK_4$ upon sensitization of mice with interferon gamma (IFNγ) and D-galactosamine[27]. Sensitization was used to mimic priming of a host defense towards further microbial challenges by an underlying infection. While mice that had received no mAb or conT2 30 min prior to injection succumbed to lethal shock within 24 h, mice treated with T2.5 survived (FIG. 6a). Intending to employ a complex challenge mimicking infection for a distinct shock model, the inventors took advantage of the finding that shock induction by viable or heat inactivated Gram-positive B. subtilis bacteria is TLR2 dependent not only in a low dose, but also in a high dose model (unpublished observation). Mice were pretreated with T2.5 or conT2 followed by challenge with a lethal dose of B. subtilis (protective protocol). In a separate group of mice, the inventors first administered B. subtilis and applied T2.5 up to 3 h later (therapeutic protocol). In the absence of T2.5 the high dose B. subtilis challenge was lethal for all mice tested (FIG. 6b). However, when given T2.5 either prior (1 h), or up to 2 h after microbial challenge, all B. subtilis challenged mice survived. Most notably, treatment with T2.5 even 3 h after potentially lethal injection saved 75% of mice challenged (FIG. 6b).

The results indicated herein show a therapeutically useful function of an antagonistic TLR2 mAb in TLR2 driven septic shock. The inventors found that application of TLR2 agonists was lethal in two experimental models of septic shock and therefore aimed at identification of antibodies blocking TLR2. Here the inventors show that the mAb T2.5 prevents $P_3CSK_4$, a synthetic analogue of bacterial lipopeptides, or Gram-positive bacteria (B. subtilis) induced shock in mice. T2.5 also blocks human TLR2 function, since subcellular NF-κB translocation upon TLR2 specific challenge of primary human macrophages was inhibited upon its application.

The lack of TLR functions negatively affects humans at least upon acute infections[28,29]. In a systemic model of polymicrobial sepsis encompassing standardized influx of the gut flora into the peritoneal cavity, however, mice benefit from the lack of TLR functions[30] indicating TLR dependent mediation of harmful effects in acute infection. Indeed, blockade or application of LPS binding proteins such as CD 14, bactericidal/permeability-increasing protein (BPI), or LPS binding protein (LBP) has been effective to inhibit LPS induced pathology[31-34] even after LPS application. Since this exemplified the prevalent role of a single cellular system for specific recognition of a microbial product[35,36], the inventors attempted to intervene in cell activation by TLR2 specific microbial products. The finding that T2.5 recognized murine and human TLR2 on the cell surface of and within cells cultured in vitro, as well as exhibited antagonistic effects upon application to cells expressing these receptors provided a basis for our attempt. Furthermore, the antagonistic function was specific and dose dependent.

The inventors analyzed the potential of T2.5 to prevent TLR2 driven immunopathology. Application of T2.5 30 min or 1 h prior to application of lethal doses of TLR2 specific agonists $P_3CSK_4$ to sensitized mice or of *B. subtilis* to normal mice, respectively, protected mice against their lethal effects (FIG. 6a and b), but not against the lethal effects of LPS (data not shown). In fact, *B. subtilis* induced shock was prevented upon application of T2.5 2 h, or even 3 h after shock induction (100% or 75% of survival, respectively). Their results indicate complement mediated depletion of TLR2$^+$ cells as an unlikely mechanism of T2.5 mediated shock prevention, since application of the mTLR2 specific isotype matched mAb conT2 in vivo did not result in protection. This implicates reversibility of mAb mediated TLR2 blockade which is potentially important for timely recovery of TLR2 dependent cellular responsiveness in later phases of sepsis at which diminished immune function is fatal[9]. The demonstration of beneficial effects of T2.5 in both, a sensitization dependent and a high dose TLR2 specific experimental model, validate a therapeutical application in the face of many animal models being restricted to one of the two respective dosages. This characteristic may improve transferability of the results from our animal study to treatment of sepsis in humans[9].

Perhaps it is the surprisingly very low constitutive surface expression of TLR2 in host cells such as CD11b$^+$ (macrophage), GR1$^+$ (granulocyte), CD19$^+$ (B cell), CD11c$^+$ (dendritic cell) splenocytes, and peritoneal cells in vivo (FIG. 4 and data not shown), which explains the efficacy of T2.5 mediated prevention of shock triggered via TLR2. This low surface expression is in contrast with relatively high surface expression in unchallenged primary murine (FIG. 1), as well as human myeloid cells upon in vitro culture[37] giving account for immediate TLR2 expression analysis ex vivo. However, comparison of TLR2-staining of non-permeabilized and permeabilized cells indicates that a major portion of TLR2 was localized in the intracellular compartment of murine CD11b$^+$ and GR1$^+$ cells, as well as human macrophages (FIG. 4c, unpublished observation and FIG. 2b). In fact, the inventors noted increased surface and intracellular TLR2 expression in specific cell populations 24 h after bacterial infection which was similar upon LPS challenge (FIG. 4 and data not shown). The time course of TLR2 regulation in distinct immune cells upon microbial contact needs to be investigated in more detail because it might determine the time frame in which TLR blockade based intervention strategies can be effective.

Antagonistic properties have recently been demonstrated in vitro also for two anti human TLR2 mAbs[38,39] possibly indicating distinct active complex formation of TLRs as compared to receptors for which agonistic antibodies have been identified. However, T2.5 interferes with the lipopeptide/TLR2 complex that induces cell activation, as well as recognizes a human TLR2 construct lacking the N-terminal third of the TLR2LRR rich domain (FIG. 17c) the inventors found to be dispensable for cellular recognition of lipopeptides[40]. Thus, the epitope recognized by T2.5 must be located within the C-terminal portion of the TLR2ECD. The inventors expect that identification of the epitope will show its conservation between mice and humans. The potential of T2.5, for instance in combination with further inhibitors of inflammatory processes, to inhibit pathogenesis of clinically important infections awaits its evaluation. In conclusion, the data provided herein are the first to point out the potential of TLR2 specific antibody application as a therapeutic strategy to block TLR2 mediated cell activation in the course of acute infection through in vivo evidence.

Methods

Material. Over night (o. n.) *B. subtilis* (DSMZ.1087) cultures containing approximately $1 \times 10^{10}$ colony forming units (cfu)/ml (brain heart medium) were used immediately or heat inactivated (h. i.) at 56° C. for 50 min. Synthetic $P_3CSK_4$ was purchased from ECHAZ microcollections (Tubingen, Germany), ultra pure LPS from *Salmonella minnesota* Re595 was from List Laboratory (Campbell, Calif.), recombinant murine IFNγ and IL-1β from Peprotech (London, England), and D-galactosamine from Sigma (Deisenhofen, Germany).

Mice. Matched groups of wild-type (TLR2$^{+/+}$) B57BL/6 and TLR2$^{-/-}$ [27] mice kindly provided by Tularik (generated by Deltagen; South San Francisco, Calif.; nine-fold crossed towards B57BL/6 background) were applied.

Generation of TLR2ECD specific antibodies and ELISA. A cDNA fragment encoding the N-terminal 587 amino acids of mTLR2[41] was amplified from a RAW264.7 cDNA library (advantage kit, BD Clontech, Heidelberg, Germany). The murine TLR2ECD was fused to a C-terminal thrombin cleavage site followed by a human IgGFcγ moiety. The murine TLR2ECD protein was purified upon overexpression in HEK293 cells and thrombin digestion. A TLR2$^{-/-}$ mouse was immunized by intraperitoneal (i. p.) injection of 50 μg of TLR2ECD and 10 nmol of a thioated DNA oligonucleotide (5'-TCCATGACGTTCCTGA-3', Tib Molbiol, Berlin, Germany) (SEQ ID NO: 5) for three times within eight weeks. Its splenocytes were fused with murine P3X cells and hybridomas were selected[42]. MAb specificities for TLR2ECD, as well as cyto- and chemokine concentrations in cell supernatants or murine sera (see below) were analyzed by ELISA (R&D systems, Minneapolis, Minn.).

Flow cytometry. Stably transfected HEK293 cell clones, as well as uninduced peritoneal wash-out macrophages were cultured o. n. as described[40]. Flow cytometry was performed upon staining with either T2.5, or affinity purified polyclonal rabbit antisera specific for the murine TLR2ECD[43] or the Flag tag (Sigma), as well as respective secondary mAbs (BD Pharmingen, Heidelberg, Germany).

For establishment of mTLR2 expression analysis in primary cells, surface and intracellular T2.5 dependent staining of CD11b$^+$ splenocytes[42] from wild-type and TLR2$^{-/-}$ mice challenged with LPS (0.5 mg, i. p., 24 h) were compared by flow cytometry (CyAn, Dako Cytomation, Fort Collins, Colo.). Cells were stained with photoactivated ethidium monoazide (Molecular Probes, Amsterdam, Netherlands) immediately upon isolation, followed by TLR2 specific surface staining, or intracellular staining (cytofix/cytoperm, BD Pharmingen). In order to analyze TLR2 expression in non- or *B. subtilis* infected ($5 \times 10^{10}$ cfu, i. p., 24 h) mice, peritoneal washout cells and splenocytes[42] from five wild-type or TLR2$^{-/-}$ mice were pooled, respectively. Fluorescence labeled cell surface marker antibodies (BD Pharmingen) and primary T2.5 stained with secondary anti mIgG1 were used as indicated.

Immunoprecipitation and immunoblot analysis. Lysates of Flag-TLR2 transfected HEK293 cells or macrophages, as well as 1 μg of antibody and protein G beads (Santa Cruz, Calif.) were mixed for o. n. precipitation. Immune complexes or cell lysates were analyzed by immunoblot analysis as described[40]. Precipitations were controlled by application of Flag specific (mAb M2, Sigma) or protein G beads only. Flag (HEK293) or mTLR2[43] (RAW264.7) specific antisera were applied for immunoblot analyses. In contrast, total lysates of macrophages (see inhibition experiments) were analyzed for phosphorylation of kinases indicated.

Cytochemical staining of TLR2 or NF-κB. Transfected HEK293 cell clones, as well as primary murine or human macrophages, the last isolated as CD 14+ peripheral blood leukocytes and cultured in 20% of autologous serum[44], were grown on slides. Cells were washed with PBS, permeabilized, and incubated with 50 μg/ml TLR2 specific mAb and/or anti NF-κB/p65 (polyclonal rabbit, Santa Cruz)[40]. Specific secondary αIgG antibodies were applied. Cell membranes were stained with labeled concanavalin A (Molecular Probes).

Inhibition of TLR2 dependent cell activation in vitro and in vivo. Transiently transfected HEK293 cells, murine RAW264.7, as well as primary macrophages were used[40]. 50 μg/ml of antibodies were applied 30 min prior to challenge with 100 ng/ml of LPS, IL-1β, $P_3CSK_4$, or $1 \times 10^6$ cfu/ml of h. i. B. subtilis. HEK293 cells were cotransfected with reporter[45], human CD14, human or mTLR2, and MD2 (provided by Tularik, Drs. Golenbock and Heine, as well as Miyake, respectively) expression plasmids, and NF-κB dependent reportergene activity was assayed after 6 h of stimulation[40]. TNFα concentrations in supernatants of RAW264.7 and primary murine macrophages, as well as NF-κB translocation in human macrophages[44] were analyzed 24 h and 90 min after challenge, respectively. For carrying out challenge and antibody dose dependent NF-κB dependent EMSA, as well as p38, Erk1/2, and Akt phosphorylation specific immunoblot analysis (Cell signaling, Frankfurt, Germany), RAW264.7 macrophages were used. $1 \times 10^6$ cells were pretreated with antibodies as described above at various concentrations and stimulated for 90 min (EMSA) or 30 min (kinase phosphorylation analysis)[40]. For analysis of TLR2 inhibition in vivo, mice were injected i. p. with 1 mg of T2.5 or left untreated. 1 h later, 100 μg of $P_3CSK_4$ and 20 mg of D-galactosamine were injected i. p. Serum concentrations of TNFα, IL-8, IL-6, and IL-12p40 in five unchallenged control mice were 0.05 ng/ml, 0.43 ng/ml, not detectable, and 0.44 ng/ml, respectively.

Systemic shock induction. In an experimental sensitization dependent model[27], mice were injected intravenously with 1.25 μg of murine IFNγ. 20 min later, mice were injected i. p. with 1 mg of mAb as indicated. 50 min after IFNγ injection, 100 μg of synthetic $P_3CSK_4$ and 20 mg of D-galactosamine were injected i. p. as well. The experimental high dose shock model encompassed a single i. p. injection of h. i. B. subtilis suspension (corresponding to $5 \times 10^{10}$ cfu) with prior (1 h) or subsequent (1 h, 2 h, or 3 h) i. p. injection of 1 mg mAb as indicated.

Figure 17:
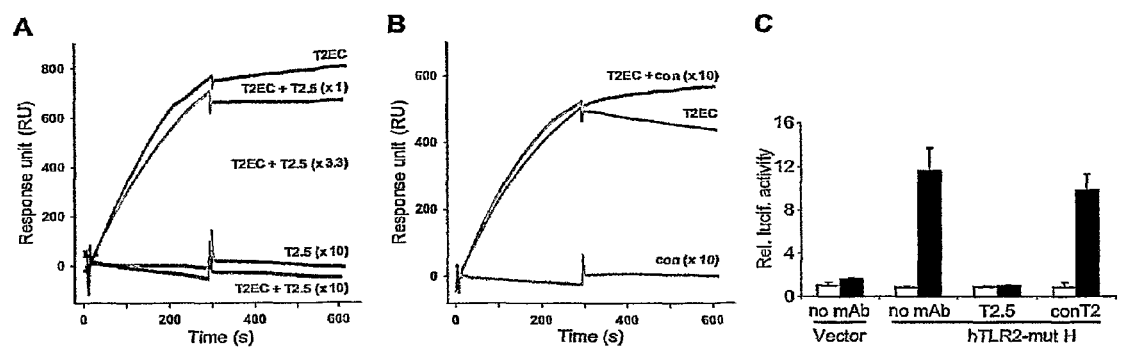

Material and Method (for FIG. 17)

Abrogation of TLR2ECD ligand-binding by T2.5 and analysis of T2.5 epitope localization. To investigate whether T2.5 blocked binding of TLR2 to its synthetic agonist $P_3CSK_4$ the inventors established a SPR biosensor based binding assay. $P_3CSK_4$ was immobilized on a chip surface and binding of T2EC was tested under various conditions. PHCSK$_4$, a non-active analogue of $P_3CSK_4$, was used as control and sensograms are displayed as subtracted binding curves. Binding of T2EC to $P_3CSK_4$ was specific (FIG. 17a). When T2EC was pre-incubated with T2.5, the antibody dose dependently inhibited T2EC-$P_3CSK_4$ binding (FIG. 17a). A molar ratio of 3.3 (T2.5:T2ECD) was required to reduce binding to 50%. Pre-incubation of T2EC with T2.5 at a 10 fold molar excess abrogated T2EC-$P_3CSK_4$ interaction (FIG. 17a). In contrast, an isotype matched control antibody did not block binding of T2EC to $P_3CSK_4$ even if applied at 10 fold molar excess (FIG. 17b). If applied alone, both mAbs did not interact with the sensor-chip surface (FIG. 17, a and b). The N-terminal third of the LRR-rich domain of human TLR2 is not involved in lipopeptide recognition (37) and T2.5 cross-reacts with human TLR2 (FIGS. 2b and 3e). Thus, we applied T2.5 to HEK293 cells overexpressing a mutant construct of human TLR2 lacking the respective portion of the wild-type ECD (37). Specific abrogation of NF-κB dependent reporter gene activation upon $P_3CSK_4$ challenge after administration of T2.5 strongly suggests localization of the epitope recognized by T2.5 within the C-terminal portion of the TLR2ECD (FIG. 17c).

Direct interaction between TLR2 and $P_3CSK_4$ was demonstrated and allowed comparison of TLR2 and TLR2-T2.5-complex affinities to this ligand. SPR analysis showed the direct and specific interaction between TLR2ECD and P3CSK$_4$, as well as a specific and dose dependent inhibition of this interaction by T2.5 (FIG. 17, a and b), indicating that binding of T2.5 masked the ligand-binding domain in TLR2. Accordingly, T2.5 antagonized not specifically $P_3CSK_4$, but also h. i. B. subtilis, PGN, LTA, and mycoplasmal macrophage activating protein induced TLR2-dependent cell activation (FIG. 3 and data not shown). Blockage was specific and dose dependent (FIG. 3). Taken together, these findings show that specific binding of ligands to a discrete site within the TLR2ECD is a prerequisite for TLR2 mediated signaling.

REFERENCES

1. Medzhitov, R. & Janeway, C. A. Innate immunity: the virtues of a nonclonal system of recognition. *Cell* 91, 295-8. (1997).
2. Takeda, K., Kaisho, T. & Akira, S. Toll-like receptors. *Annu Rev Immunol* 21, 335-76 (2003).
3. Raetz, C. R. et al. Gram-negative endotoxin: an extraordinary lipid with profound effects on eukaryotic signal transduction. *Faseb J* 5, 2652-60. (1991).
4. Ulevitch, R. J. & Tobias, P. S. Receptor-dependent mechanisms of cell stimulation by bacterial endotoxin. *Annu Rev Immunol* 13, 437-57. (1995).
5. Beutler, B. & Rietschel, E. T. Timeline: Innate immune sensing and its roots: the story of endotoxin. *Nat Rev Immunol* 3, 169-76 (2003).
6. Sparwasser, T. et al. Bacterial DNA causes septic shock. *Nature* 386, 336-7 (1997).
7. Cohen, J. The immunopathogenesis of sepsis. *Nature* 420, 885-91 (2002).
8. Martin, G. S., Mannino, D. M., Eaton, S. & Moss, M. The epidemiology of sepsis in the United States from 1979 through 2000. *N Engl J Med* 348, 1546-54 (2003).
9. Hotchkiss, R. S. & Karl, I. E. The pathophysiology and treatment of sepsis. *N Engl J Med* 348, 138-50 (2003).
10. Wright, S. D., Ramos, R. A., Tobias, P. S., Ulevitch, R. J. & Mathison, J. C. CD14, a receptor for complexes of lipopolysaccharide (LPS) and LPS binding protein. *Science* 249, 1431-3. (1990).
11. Schimke, J., Mathison, J., Morgiewicz, J. & Ulevitch, R. J. Anti-CD14 mAb treatment provides therapeutic benefit after in vivo exposure to endotoxin. *Proc Nall Acad Sci USA* 95, 13875-80 (1998).
12. Wang, H. et al. HMG-1 as a late mediator of endotoxin lethality in mice. *Science* 285, 248-51 (1999).

13. Jin, H. et al. Protection against rat endotoxic shock by p55 tumor necrosis factor (TNF) receptor immunoadhesin: comparison with anti-TNF monoclonal antibody. *J Infect Dis* 170, 1323-6 (1994).
14. Yoon, D. Y. & Dinarello, C. A. Antibodies to domains II and III of the IL-1 receptor accessory protein inhibit IL-1 beta activity but not binding: regulation of IL-1 responses is via type I receptor, not the accessory protein. *J Immunol* 160, 3170-9 (1998).
15. Marshall, J. C. Such stuff as dreams are made on: mediator-directed therapy in sepsis. *Nat Rev Drug Discov* 2, 391-405 (2003).
16. Ito, H. Anti-interleukin-6 therapy for Crohn's disease. *Curr Pharm Des* 9, 295-305 (2003).
17. Reimold, A. M. New indications for treatment of chronic inflammation by TNF-alpha blockade. *Am J Med Sci* 325, 75-92 (2003).
18. Dziarski, R., Jin, Y. P. & Gupta, D. Differential activation of extracellular signal-regulated kinase (ERK) 1, ERK2, p38, and c-Jun NH2-terminal kinase mitogen-activated protein kinases by bacterial peptidoglycan. *J Infect Dis* 174, 777-85. (1996).
19. Kengatharan, K. M., De Kimpe, S., Robson, C., Foster, S. J. & Thiemermann, C. Mechanism of gram-positive shock: identification of peptidoglycan and lipoteichoic acid moieties essential in the induction of nitric oxide synthase, shock, and multiple organ failure. *J Exp Med* 188, 305-15 (1998).
20. Schleifer, K. H. & Kandler, O. Peptidoglycan types of bacterial cell walls and their taxonomic implications. *Bacteriol Rev* 36, 407-77. (1972).
21. Fischer, W. Phosphocholine of pneumococcal teichoic acids: role in bacterial physiology and pneumococcal infection. *Res Microbiol* 151, 421-7. (2000).
22. Fan, X. et al. Structures in *Bacillus subtilis* are recognized by CD14 in a lipopolysaccharide binding protein-dependent reaction. *Infect Immun* 67, 2964-8. (1999).
23. Bessler, W. G., Johnson, R. B., Wiesmuller, K. & Jung, G. B-lymphocyte mitogenicity in vitro of a synthetic lipopeptide fragment derived from bacterial lipoprotein. *Hoppe Seylers Z Physiol Chem* 363, 767-70 (1982).
24. Mitsuzawa, H. et al. Extracellular Toll-like receptor 2 region containing Ser40-Ile64 but not Cys30-Ser39 is critical for the recognition of *Staphylococcus aureus* peptidoglycan. *J Biol Chem* 276, 41350-6 (2001).
25. Rock, F. L., Hardiman, G., Timans, J. C., Kastelein, R. A. & Bazan, J. F. A family of human receptors structurally related to *Drosophila* Toll. *Proc Natl Acad Sci USA* 95, 588-93, (1998).
26. Freudenberg, M. A. & Galanos, C. Tumor necrosis factor alpha mediates lethal activity of killed gram-negative and gram-positive bacteria in D-galactosamine-treated mice. *Infect Immun* 59, 2110-5 (1991).
27. Werts, C. et al. Leptospiral lipopolysaccharide activates cells through a TLR2-dependent mechanism. *Nat Immunol* 2, 346-52. (2001).
28. Picard, C. et al. Pyogenic bacterial infections in humans with IRAK-4 deficiency. *Science* 299, 2076-9 (2003).
29. Medvedev, A. E. et al. Distinct Mutations in IRAK-4 Confer Hyporesponsiveness to Lipopolysaccharide and Interleukin-1 in a Patient with Recurrent Bacterial Infections. *J Exp Med* 198, 521-31 (2003).
30. Weighardt, H. et al. Cutting edge: myeloid differentiation factor 88 deficiency improves resistance against sepsis caused by polymicrobial infection. *J Immunol* 169, 2823-7 (2002).
31. Gallay, P., Heumann, D., Le Roy, D., Barras, C. & Glauser, M. P. Mode of action of anti-lipopolysaccharide-binding protein antibodies for prevention of endotoxemic shock in mice. *Proc Natl Acad Sci USA* 91, 7922-6 (1994).
32. Lamping, N. et al. LPS-binding protein protects mice from septic shock caused by LPS or gram-negative bacteria. *J Clin Invest* 101, 2065-71 (1998).
33. Dankesreiter, S., Hoess, A., Schneider-Mergener, J., Wagner, H. & Miethke, T. Synthetic endotoxin-binding peptides block endotoxin-triggered TNF-alpha production by macrophages in vitro and in vivo and prevent endotoxin-mediated toxic shock. *J Immunol* 164, 4804-11 (2000).
34. Levin, M. et al. Recombinant bactericidal/permeability-increasing protein (rBPI21) as adjunctive treatment for children with severe meningococcal sepsis: a randomised trial. rBPI21 Meningococcal Sepsis Study Group. *Lancet* 356, 961-7 (2000).
35. Gray, P. W. et al. Cloning of the cDNA of a human neutrophil bactericidal protein. Structural and functional correlations. *J Biol Chem* 264, 9505-9. (1989).
36. Jin, H. et al. Protection against endotoxic shock by bactericidal/permeability-increasing protein in rats. *J Clin Invest* 95, 1947-52 (1995).
37. Krutzik, S. R. et al. Activation and regulation of Toll-like receptors 2 and 1 in human leprosy. *Nat Med* 9, 525-532 (2003).
38. Brightbill, H. D. et al. Host defense mechanisms triggered by microbial lipoproteins through toll-like receptors. *Science* 285, 732-6. (1999).
39. Flo, T. H. et al. Human toll-like receptor 2 mediates monocyte activation by *Listeria monocytogenes*, but not by group B streptococci or lipopolysaccharide. *J Immunol* 164, 2064-9. (2000).
40. Meng, G. et al. Cellular recognition of tri-/di-palmitoylated peptides is independent from a domain encompassing the N-terminal seven leucine rich repeat (LRR)/LRR-like motifs of TLR2. *J Biol Chem* 14, 14 (2003).
41. Heine, H. et al. Cutting edge: cells that carry A null allele for toll-like receptor 2 are capable of responding to endotoxin. *J Immunol* 162, 6971-5. (1999).
42. Coligan, J. E., Kruisbeek, A. M., Margulies, D. H., Shevach, E. M. & Strobe, W. *Current Protocols in Immunology*, (John Wiley & Sons, Inc., New York, 1990).
43. Sing, A. et al. *Yersinia* V-antigen exploits toll-like receptor 2 and CD14 for interleukin 10-mediated immunosuppression. *J Exp Med* 196, 1017-24 (2002).
44. Linder, S., Nelson, D., Weiss, M. & Aepfelbacher, M. Wiskott-Aldrich syndrome protein regulates podosomes in primary human macrophages. *Proc Natl Acad Sci USA* 96, 9648-53 (1999).
45. Schindler, U., & Baichwal, V. R. Three NF-kappa B binding sites in the human E-selectin gene required for maximal tumor necrosis factor alpha-induced expression. *Mol Cell Biol* 14, 5820-31 (1994).

The invention claimed is:

1. An isolated cross-reactive antibody or a fragment thereof, which specifically inhibits or blocks mammalian Toll-like Receptor 2 (TLR2)-mediated immune cell activation by specifically binding to the C-terminal portion of the extracellular domains of at least human and murine TLR2, wherein the antibody or fragment thereof specifically binds through the variable regions of the heavy and light chains, wherein the heavy chain variable region comprises a complementarity determining region 1 (CDR1) region wherein the amino acid sequence of the CDR1 region comprises Gly-Phe-Thr-Phe-Thr-Thr-Tyr-Gly (residues 58-65 of SEQ ID NO:6), a CDR2 region wherein the amino acid sequence of the CDR2 region comprises Ile-Tyr-Pro-Arg-Asp-Gly-Ser-Thr (residues 83-90 of SEQ ID NO: 6) and a CDR3 region wherein the amino acid sequence of the CDR3 region comprises Ala-Arg-Leu-Thr-Gly-Gly-Thr-Phe-Leu-Asp-Tyr (residues 129-139 of SEQ ID NO:6), and wherein the light chain variable region comprises a CDR1 region wherein the amino acid sequence of the CDR1 region comprises Glu-Ser-Val-Glu-Tyr-Tyr-Gly-Thr-Ser-Leu (residues 47-56 of SEQ ID NO:7), a CDR2 region wherein the amino acid sequence of the CDR2 region comprises Gly-Ala-Ser (residues 74-76 of SEQ ID NO:7) and a CDR3 region wherein the amino acid sequence of the CDR3 region comprises Gln-Gln-Ser-Arg-Lys-Leu-Pro-Trp-Thr (residues 113-121 of SEQ ID NO:7), wherein the CDRs are identified by the IMGT database.

2. The antibody or antibody fragment of claim 1, wherein the antibody is selected from the group consisting of a polyclonal antibody, a monoclonal antibody, a humanised antibody, a chimeric antibody and a synthetic antibody.

3. The antibody or fragment thereof of claim 1 wherein the antibody comprises:

a heavy chain variable region having the amino acid sequence of SEQ ID NO:6;
a light chain variable region having the amino acid sequence of SEQ ID NO:7; or both.

4. The antibody fragment of claim 1 comprising complementarity determining regions (CDRs) of the heavy chain variable domain, wherein the amino acid sequence of the CDR1 region comprises Gly-Phe-Thr-Phe-Thr-Thr-Tyr-Gly (residues 58-65 of SEQ ID NO:6), the amino acid sequence of the CDR2 region comprises Ile-Tyr-Pro-Arg-Asp-Gly-Ser-Thr (residues 83-90 of SEQ ID NO:6) and the amino acid sequence of the CDR3 region comprises Ala-Arg-Leu-Thr-Gly-Gly-Thr-Phe-Leu-Asp-Tyr (residues 129-139 of SEQ ID NO:6), and the complementarity determining regions (CDRs) of the light chain variable domain, wherein the amino acid sequence of the CDR1 region comprises Glu-Ser-Val-Glu-Tyr-Tyr-Gly-Thr-Ser-Leu (residues 47-56 of SEQ ID NO:7), the amino acid sequence of the CDR2 region comprises Gly-Ala-Ser (residues 74-76 of SEQ ID NO:7) and the amino acid sequence of the CDR3 region comprises Gln-Gln-Ser-Arg-Lys-Leu-Pro-Trp-Thr (residues 113-121 of SEQ ID NO:7), wherein the CDRs are identified by the IMGT database.

5. The antibody fragment of claim 1 wherein the antibody fragment is selected from the group consisting of a Fab antibody fragment, a F(ab')2 antibody fragment and an Fv antibody fragment.

6. An isolated nucleic acid, which comprises nucleic acids Nos. 172-195, 247-270 and 385-417 of SEQ ID NO:1; nucleic acids Nos. 139-168, 220-228 and 337-363 of SEQ ID NO:2; or both nucleic acids Nos. 172-195, 247-270 and 385-417 of SEQ ID NO:1 and nucleic acids Nos. 139-168, 220-228 and 337-363 of SEQ ID NO:2.

7. The isolated nucleic acid of claim 6, said isolated nucleic acid further comprising a nucleic acid encoding one or more regulatory sequences operably linked thereto.

8. An isolated cross-reactive antibody or a fragment thereof, which specifically inhibits or blocks mammalian Toll-like Receptor 2 (TLR2)-mediated immune cell activation by specifically binding to the C-terminal portion of the extracellular domains of at least human and murine TLR2, wherein the antibody or fragment thereof specifically binds through the variable regions of the heavy and light chains, wherein the heavy chain variable region comprise a complementarity determining region 1 (CDR1) region wherein the amino acid sequence of the CDR1 region comprises Thr-Tyr-Gly-Ile-Asn (residues 63-67 of SEQ ID NO:6), a CDR2 region wherein the amino acid sequence of the CDR2 region comprises Trp-Ile-Tyr-Pro-Arg-Asp-Gly-Ser-Thr-Asn-Phe-Asn-Glu-Asn-Phe-Lys-Asp (residues 82-98 of SEQ ID NO: 6), and a CDR3 region wherein the amino acid sequence of the CDR3 region comprises Ala-Arg-Leu-Thr-Gly-Gly-Thr-Phe-Leu-Asp-Tyr (residues 129-139 of SEQ ID NO:6), and wherein the light chain variable region comprises a CDR1 region wherein the amino acid sequence of the CDR1 region comprises Arg-Ala-Ser-Glu-Ser-Val-Glu-Tyr-Tyr-Gly-Thr-Ser-Leu-Met-Gln (residues 44-58 of SEQ ID NO:7), a CRD2 region wherein the amino acid sequence of the CDR2 region comprises Gly-Ala-Ser-Asn-Val-Glu-Ser (residues 74-80 of SEQ ID NO:7) and a CDR3 region wherein the amino acid sequence of the CDR3 region comprises Gln-Gln-Ser-Arg-Lys-Leu-Pro-Trp-Thr (residues 113-121 of SEQ ID NO:7).

9. The antibody or antibody fragment of claim 8, wherein the antibody is selected from the group consisting of a polyclonal antibody, a monoclonal antibody, a humanised antibody, a chimeric antibody and a synthetic antibody.

10. The antibody or fragment thereof of claim 8, wherein the antibody comprises:
a heavy chain variable region having the amino acid sequence of SEQ ID NO:6;
a light chain variable region having the amino acid sequence of SEQ ID NO:7; or both.

11. The antibody fragment of claim 8 comprising complementarity determining regions (CDRs) of the heavy chain variable domain, wherein the amino acid sequence of the CDR1 region comprises Thr-Tyr-Gly-Ile-Asn (residues 63-67 of SEQ ID NO:6), the amino acid sequence of the CDR2 region comprises Trp-Ile-Tyr-Pro-Arg-Asp-Gly-Ser-Thr-Asn-Phe-Asn-Glu-Asn-Phe-Lys-Asp (residues 82-98 of SEQ ID NO: 6), and the amino acid sequence of the CDR3 region comprises Ala-Arg-Leu-Thr-Gly-Gly-Thr-Phe-Leu-Asp-Tyr (residues 129-139 of SEQ ID NO:6), and the complementarity determining regions (CDRs) of the light chain variable domain, wherein the amino acid sequence of the CDR1 region comprises Arg-Ala-Ser-Glu-Ser-Val-Glu-Tyr-Tyr-Gly-Thr-Ser-Leu-Met-Gln (residues 44-58 of SEQ ID NO:7), the amino acid sequence of the CDR2 region comprises Gly-Ala-Ser-Asn-Val-Glu-Ser (residues 74-80 of SEQ ID NO:7) and the amino acid sequence of the CDR3 region comprises Gln-Gln-Ser-Arg-Lys-Leu-Pro-Trp-Thr (residues 113-121 of SEQ ID NO:7).

12. The antibody fragment of claim 8 wherein the antibody fragment is selected from the group consisting of a Fab antibody fragment, a F(ab')2 antibody fragment and an Fv antibody fragment.

13. An isolated nucleic acid, which comprises nucleic acids Nos. 187-201, 244-294 and 385-417 of SEQ ID NO:1; nucleic acids Nos. 130-174, 220-240 and 337-363 of SEQ ID NO:2; or both nucleic acids Nos. 187-201, 244-294 and 385-417 of SEQ ID NO:1 and nucleic acids Nos. 130-174, 220-240 and 337-363 of SEQ ID NO:2.

14. The isolated nucleic acid of claim 13, said isolated nucleic acid further comprising a nucleic acid encoding one or more regulatory sequences operably linked thereto.

15. An isolated cross-reactive antibody or a fragment thereof, which specifically inhibits or blocks mammalian Toll-like Receptor 2 (TLR2)-mediated immune cell activation by specifically binding to the C-terminal portion of the extracellular domains of at least human and murine TLR2, wherein the antibody or fragment thereof specifically binds through the variable regions of the heavy and light chains, wherein the heavy chain variable region comprises amino acid residues Nos. 58-65 (Gly-Phe-Thr-Phe-Thr-Thr-Tyr-Gly), amino acid residues Nos. 83-90 (Ile-Tyr-Pro-Arg-Asp-Gly-Ser-Thr) and amino acid residues Nos. 129-139 (Ala-Arg-Leu-Thr-Gly-Gly-Thr-Phe-Leu-Asp-Tyr) of SEQ ID NO:6, and wherein the light chain variable region comprises amino acid residues Nos. 47-56 (Glu-Ser-Val-Glu-Tyr-Tyr-Gly-Thr-Ser-Leu), amino acid residues Nos. 74-76 (Gly-Ala-Ser) and amino acid residues Nos. 113-121 (Gln-Gln-Ser-Arg-Lys-Leu-Pro-Trp-Thr) of SEQ ID NO:7.

16. The antibody or antibody fragment of claim 15, wherein the antibody is selected from the group consisting of a polyclonal antibody, a monoclonal antibody, a humanised antibody, a chimeric antibody and a synthetic antibody.

17. The antibody fragment of claim 15 comprising amino acid residues Nos. 58-65 (Gly-Phe-Thr-Phe-Thr-Thr-Tyr-Gly), amino acid residues Nos. 83-90 (Ile-Tyr-Pro-Arg-Asp-Gly-Ser-Thr) and amino acid residues Nos. 129-139 (Ala-Arg-Leu-Thr-Gly-Gly-Thr-Phe-Leu-Asp-Tyr) of SEQ ID NO:6, and amino acid residues Nos. 47-56 (Glu-Ser-Val-Glu-Tyr-Tyr-Gly-Thr-Ser-Leu), amino acid residues Nos. 74-76 (Gly-Ala-Ser) and amino acid residues Nos. 113-121 (Gln-Gln-Ser-Arg-Lys-Leu-Pro-Trp-Thr) of SEQ ID NO:7.

18. The antibody fragment of claim 15 wherein the antibody fragment is selected from the group consisting of a Fab antibody fragment, a F(ab')2 antibody fragment and an Fv antibody fragment.

* * * * *

SEQUENCE LISTING

<160> NUMBER OF SEQ ID NOS: 7

<210> SEQ ID NO 1
<211> LENGTH: 501
<212> TYPE: DNA
<213> ORGANISM: Mus sp.

<400> SEQUENCE: 1

| | |
|---|---|
| atgtcctctc cacagtccct gaagacactg attctaacca tgggatggag ctggatcttt | 60 |
| ctcttcctcc tgtcaggaac tgcaggtgtc cactcccagg ttcagctgca gcagtctgga | 120 |
| cctgagctgg tgaaccctgg ggcgtcagtg aagttgtcct gcaaggcttc tggcttcacc | 180 |
| ttcacaacct acggtataaa ctgggtgaag caggggcctg acagggact tgagtggatt | 240 |
| ggatggattt atcctagaga tggtagtact aacttcaatg agaatttcaa ggacaaggcc | 300 |
| gcattgactg tagacacatc ctccagcaca gcgtacatgg aactccacag cctgacatct | 360 |
| gaagactctg cggtctattt ctgtgcaaga ctgactggtg ggacattcct tgactattgg | 420 |
| ggccagggca ccactctcac agtctcctca gccaaaacga cacccccatc tgtctatcca | 480 |
| ctggcccctg gatctgctgc c | 501 |

<210> SEQ ID NO 2
<211> LENGTH: 443
<212> TYPE: DNA
<213> ORGANISM: Mus sp.

<400> SEQUENCE: 2

| | |
|---|---|
| atggagtcag acacactcct gctatgggtg ctgctgctct gggttccagg ctccactggt | 60 |
| gacattgtgc tcacccaatc tccagcttct ttggctgtgt ctctagggca gagagccacc | 120 |
| atctcctgca gagccagtga aagtgttgaa tattatggca caagtttaat gcagtggtac | 180 |
| caacagaaac caggacagcc acccaaactc ctcatctttg gtgcatccaa cgtagaatct | 240 |
| ggggtccctg tcaggttcag tggcagtggg tctgggacag acttcagcct caacatccat | 300 |
| cctgtggagg aggatgatat tgtaatgtat ttctgtcagc aaagtaggaa acttccgtgg | 360 |
| acgttcggtg aggcaccaa gctggaaatc aaacgggctg atgctgcacc aactgtatcc | 420 |
| atcttcccac catccagtga gca | 443 |

<210> SEQ ID NO 3
<211> LENGTH: 537
<212> TYPE: DNA
<213> ORGANISM: Mus sp.

<400> SEQUENCE: 3

| | |
|---|---|
| catggactga aggagtagaa agacaaccta tggccaatgt cctctccaca gtccctgaag | 60 |
| acactgattc taaccatggg atggagctgg atctttctct tcctcctgtc aggaactgca | 120 |
| ggtgtccact cccaggttca gctgcagcag tctggacctg agctggtgaa ccctggggcg | 180 |
| tcagtgaagt tgtcctgcaa ggcttctggc ttcaccttca aacctacgg tataaactgg | 240 |
| gtgaagcagg gcctggaca gggacttgag tggattggat ggatttatcc tagagatggt | 300 |
| agtactaact tcaatgagaa tttcaaggac aaggccgcat tgactgtaga cacatcctcc | 360 |
| agcacagcgt acatggaact ccacagcctg acatctgaag actctgcggt ctatttctgt | 420 |
| gcaagactga ctggtgggac attccttgac tattggggcc agggcaccac tctcacagtc | 480 |
| tcctcagcca aaacgacacc cccatctgtc tatccactgg cccctggatc tgctgcc | 537 |

<210> SEQ ID NO 4
<211> LENGTH: 487
<212> TYPE: DNA
<213> ORGANISM: Mus sp.

<400> SEQUENCE: 4

```
catggactga aggagtagaa aatcctctca tctagctctc agagatggag tcagacacac      60
tcctgctatg ggtgctgctg ctctgggttc caggctccac tggtgacatt gtgctcaccc     120
aatctccagc ttctttggct gtgtctctag ggcagagagc caccatctcc tgcagagcca     180
gtgaaagtgt tgaatattat ggcacaagtt taatgcagtg gtaccaacag aaaccaggac     240
agccacccaa actcctcatc tttggtgcat ccaacgtaga atctggggtc cctgtcaggt     300
tcagtggcag tgggtctggg acagacttca gcctcaacat ccatcctgtg gaggaggatg     360
atattgtaat gtatttctgt cagcaaagta ggaaacttcc gtggacgttc ggtgaggca     420
ccaagctgga aatcaaacgg gctgatgctg caccaactgt atccatcttc ccaccatcca     480
gtgagca                                                               487
```

<210> SEQ ID NO 5
<211> LENGTH: 16
<212> TYPE: DNA
<213> ORGANISM: artificial
<220> FEATURE:
<223> OTHER INFORMATION: oligonucleotide

<400> SEQUENCE: 5

```
tccatgacgt tcctga                                                      16
```

<210> SEQ ID NO 6
<211> LENGTH: 167
<212> TYPE: PRT
<213> ORGANISM: Mus sp.

<400> SEQUENCE: 6

```
Met Ser Ser Pro Gln Ser Leu Lys Thr Leu Ile Leu Thr Met Gly Trp
1               5                   10                  15

Ser Trp Ile Phe Leu Phe Leu Leu Ser Gly Thr Ala Gly Val His Ser
            20                  25                  30

Gln Val Gln Leu Gln Gln Ser Gly Pro Glu Leu Val Asn Pro Gly Ala
        35                  40                  45

Ser Val Lys Leu Ser Cys Lys Ala Ser Gly Phe Thr Phe Thr Thr Tyr
    50                  55                  60

Gly Ile Asn Trp Val Lys Gln Gly Pro Gly Gln Gly Leu Glu Trp Ile
65                  70                  75                  80

Gly Trp Ile Tyr Pro Arg Asp Gly Ser Thr Asn Phe Asn Glu Asn Phe
                85                  90                  95

Lys Asp Lys Ala Ala Leu Thr Val Asp Thr Ser Ser Ser Thr Ala Tyr
            100                 105                 110

Met Glu Leu His Ser Leu Thr Ser Glu Asp Ser Ala Val Tyr Phe Cys
        115                 120                 125

Ala Arg Leu Thr Gly Gly Thr Phe Leu Asp Tyr Trp Gly Gln Gly Thr
    130                 135                 140

Thr Leu Thr Val Ser Ser Ala Lys Thr Thr Pro Pro Ser Val Tyr Pro
145                 150                 155                 160

Leu Ala Pro Gly Ser Ala Ala
                165
```

```
<210> SEQ ID NO 7
<211> LENGTH: 147
<212> TYPE: PRT
<213> ORGANISM: Mus sp.

<400> SEQUENCE: 7

Met Glu Ser Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Glu Tyr Tyr Gly Thr Ser Leu Met Gln Trp Tyr Gln Gln Lys Pro
    50                  55                  60

Gly Gln Pro Pro Lys Leu Leu Ile Phe Gly Ala Ser Asn Val Glu Ser
65                  70                  75                  80

Gly Val Pro Val Arg Phe Ser Gly Ser Gly Ser Gly Thr Asp Phe Ser
                85                  90                  95

Leu Asn Ile His Pro Val Glu Glu Asp Asp Ile Val Met Tyr Phe Cys
                100                 105                 110

Gln Gln Ser Arg Lys Leu Pro Trp Thr Phe Gly Gly Gly Thr Lys Leu
            115                 120                 125

Glu Ile Lys Arg Ala Asp Ala Ala Pro Thr Val Ser Ile Phe Pro Pro
    130                 135                 140

Ser Ser Glu
145
```